United States Patent
Connor et al.

(10) Patent No.: US 10,413,518 B2
(45) Date of Patent: Sep. 17, 2019

(54) CYP450 LIPID METABOLITES REDUCE INFLAMMATION AND ANGIOGENESIS

(71) Applicant: Massachusetts Eye and Ear Infirmary, Boston, MA (US)

(72) Inventors: Kip M. Connor, Newton, MA (US); Ryoji Yanai, Cambridge, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 0 days.

(21) Appl. No.: 15/684,251

(22) Filed: Aug. 23, 2017

(65) Prior Publication Data
US 2018/0133187 A1 May 17, 2018

Related U.S. Application Data

(62) Division of application No. 14/758,724, filed as application No. PCT/US2014/010880 on Jan. 9, 2014, now Pat. No. 9,770,426.

(60) Provisional application No. 61/751,617, filed on Jan. 11, 2013.

(51) Int. Cl.
*A61K 31/202* (2006.01)
*A61K 31/336* (2006.01)
*A61K 9/00* (2006.01)

(52) U.S. Cl.
CPC .......... *A61K 31/202* (2013.01); *A61K 9/0048* (2013.01); *A61K 31/336* (2013.01)

(58) Field of Classification Search
CPC .............................. A61K 31/202; A61K 31/336
See application file for complete search history.

(56) References Cited

U.S. PATENT DOCUMENTS 9,314,445 B2   4/2016   Georgiou

FOREIGN PATENT DOCUMENTS

| AU | 2012/307524 | 3/2013 |
| CA | 2845868 | 3/2013 |
| EA | 200701100 A1 | 10/2007 |
| EP | 2755647 | 7/2014 |
| JP | A-H5-286956 | 11/1993 |
| JP | H05286956 | 11/1993 |
| WO | WO 2006/055965 A2 | 5/2006 |
| WO | WO 2012/023254 A1 | 2/2012 |
| WO | WO 2013/037794 | 3/2013 |

OTHER PUBLICATIONS

Arnold et al., "Arachidonic Acid-Metabolizing Cytochrome P450 Enzymes are Targets of Omega-3 Fatty Acids," J. Biol. Chem, Oct. 2010, 285:32720-32733.
Bazan, "Homeostatic regulation of photoreceptor cell integrity: significance of the potent mediator neuroprotection D1 biosynthesized from docosahexaenoic acid: the Proctor Lecture," Invest. Ophthalmol. Vis. Sci., 2007, 48:4866-4881.
Beebe et al., "Pharmacological characterization of CP-547,632, a novel vascular endothelial growth factor receptor-2 tyrosine kinase inhibitor for cancer therapy," Cancer Res., 2003, 63:7301-7309.
C. Morisseau et al., "Naturally occurring monoepoxides of eicosapentaenoic acid and docosahexaenoic acid are bioactive antihyperalgesic lipids," Journal of Lipid Research, 2010, 51(12):3481-3490.
Cao et al., "The extent and severity of vascular leakage as evidence of tumor aggressiveness in high-grade gliomas," Cancer Res, Sep. 2006, 66:8912-8917.
Caroline Morin et al., "17,18-Epoxyeicosatetraenoic Acid Targets PPAR [gamma] and p38 Mitogen-Activated Protein Kinase to mediate its anti-inflammatory effects in the lung," American Journal of Respiratory Cell and Molecular Biology, 2010, 43(5): 564-575.
Chew et al., "The Age-Related Eye Disease Study 2 (AREDS2) Research Group," J. Am. Med. Assoc., 2013, 309(19)10:2005-2015.
Chew, "Fatty acids and retinopathy," N. Engl. J. Med, 2011, 364:1970-1971.
Connor et al., "Increased dietary intake of omega-3 polyunsaturated fatty acids reduces pathological retinal angiogenesis," Nat. Med., 2007, 13:868-873.
Curcio et al., "Histochemistry and lipid profiling combine for insights into aging and age-related maculpathy," Methods Mol. Bio., 2009, 580:267-281.
European Communication in Application No. 14737722.0, dated Nov. 14, 2017, 7 pages.
European Search Report, Application No. 14737722.0, dated Aug. 3, 2016, 10 pages.
Goodman et al., "Approval summary: sunitinib for the treatment of imatinib refractory or intolerant gastrointestinal stromal tumors and advanced renal cell carcinoma," Clin Cancer Res., 2007, 13;1367-1373.
Gragoudas et al., "Pegaptanib for neovascular age-related macular degeneration," N. Engl. J. Med, 2004, 351:2805-2816.
Im et al., "Omega-3 fatty acids in anti-inflammation (pro-resolution) and GPCRs," Prog Lipid Res., 2012, 51:232-237.
International Preliminary Report on Patentability in International Application No. PCT/US2014/010880, dated Jul. 14, 2015, 7 pages.
International Search Report and Written Opinion in International Application No. PCT/US2014/010880, dated May 7, 2014, 9 pages.
Ishida et al., "Leukocytes mediate retinal vascular remodeling during development and vaso-obliteration in disease," Nature Med, 2003, 9:781-788.
Kane et al., "Sorafenib for the treatment of advanced renal cell carcinoma," Clin Cancer Res., 2006, 12;7271-7278.
Kang et al., "The role of the tissure omega6/omega-3 fatty acid ration in regulating tumor angiogenesis," Cancer Metast. Rev., Jun. 2013, 32(1-2):201-210.

(Continued)

*Primary Examiner* — Sahar Javanmard
(74) *Attorney, Agent, or Firm* — Fish & Richardson P.C.

(57) ABSTRACT

Methods for reducing angiogenesis, inflammation, and vascular permeability in a subject by administering an epoxymetabolite of Docosahexaenoic acid (DHA) and Eicosapentaenoic acid (EPA), e.g., as listed in Table A, e.g., one or both of 17,18-epoxyeicosatetraenoic acid (EEQ) and 19,20-epoxydocosapentaenoic acid (EDP), e.g., for the treatment of conditions associated with inflammation or excess angiogenesis or neovascularization, including age-related macular degeneration, cancer, stroke, and arthritis.

3 Claims, 28 Drawing Sheets

(56) References Cited

OTHER PUBLICATIONS

Lee et al., "Vascular permeability precedes spontaneous intracerebral hemorrhage in stroke-prone spontaneously hypertensive rats," Stroke, 2007, 38:3289-3291.
Lin et al., "Measuring elevated microvascular permeability and predicting hemorrhagic transformation in acute ischemic stroke using first-pass dynamic perfusion CT imaging," AJNR, Aug. 2007, 28:1292-1298.
Ng and Adamis, "Anti-VEGF aptamer (pegaptanib) therapy for ocular vascular diseases," Ann. N.Y. Acad. Sci., 2006, 1082:151-171.
Office Action in Japanese Application No. 2015-552772, dated Sep. 12, 2017, 8 pages (with English translation).
Office Action in Australian Application No. 2014205369, dated Oct. 24, 2017.
Pei H Cui et al., "The [omega]-3 epoxide of eicosapentaenoic acid inhibits endothelial cell proliferation by p38 MAP kinase activation and cyclin D1/CDK4 down-regulation," British Journal of Pharmacology, 2011, 162(5):1143-1155.
Rosenfeld et al., "Ranibizumab for neovascular age-related macular degeneration," N. Engl. J. Med., 2006, 355:1419-1431.
Ruggeri et al., "CEP-7055: a novel, orally active pan inhibitor of vascular endothelial growth factor receptor tyrosine kinases with potent antiangiogenic activity and antitumor efficacy in preclinical models," Cancer Res., 2003, 63:5978-5991.
SanGiovanni and Chew, "The role of omega-3 long-chain polyunsaturated fatty acids in health and disease of the retina," Prog. Retin. Eye Res., 2005, 24:87-138.
SanGiovanni et al., "The relationship of dietary lipid intake and age-related macular degeneration in a case-control study: AREDS Report No. 20," Arch. Ophthalmol., 2007, 125:671-679.
SanGiovanni et al., "The relationship of dietary omega-3 long-chain polyunsaturated fatty acid intake with incident age-related macular degeneration: AREDS Report No. 23," Arch. Ophthalmol., 2008, 126:1274-1279.
SanGiovanni et al., "ω-3 Long-chain polyunsaturated fatty acid intake and 12-y incidence of neovascular age-related macular degeneration and central geography atrophy: AREDS Report No. 30, a prospective cohort study from the Age-Related Eye Disease Study," Am. J. Clin. Nutr., 2009, 90:1601-1607.
Sapieha et al., "5-Lipoxgenase metabolite 4-HDHA is a mediator of the antiangiogenic effect of omega-3 polyunsaturated fatty acids," Sci. Transl. Med., 2011, 3:69ra12.
Sheets et al., "Neuroprotectin D1 attenuates laser-induced choroidal neovascularization in mouse," Mol Vis., 2010, 16:320-329.
Souied et al., "Oral docosahexaenoic acid in the prevention of exudative age-related macular degeneration: the Nutritional AMD Treatment 2 study," OPHTHA, 2013, 120(8):1619-1631.
Stahl et al., "Short communication: PPAR gamma mediates a direct antiangiogenic effect of omega 3-PUFAs in proliferative retinopathy," Circ. Res., 2010, 107:495-500.
Third Party Protest Against Canadian Patent Application No. 2930987, dated Nov. 24, 2017, 5 pages.
Trevor A. Mori et al., "Omega-3 fatty acids and inflammation," Current Atherosclerosis reports, 2004, 6(6):461-467.
Wang et al., "Abundant lipid and protein components of drusen," PLoS One, 2010, 5:e10329.
Wood et al., "PTK787/ZK 222584, a novel and potent inhibitor of vascular endothelial growth factor receptor tyrosine kinases, impairs vascular endothelial growth factor-induced responses and tumor growth after oral administration," Cancer Res., 2000, 60:2178-2189.
Yanai et al., "Cytochrome P450-generated metabolites derived from [omega]-3 fatty acids attenuate neovascularization," PNAS, 2014, 111(26): 9603-9608.
Yoshida et al., "Regulation of VEGF and MCP-1 expression in human retinal pigment epithelial cells by treatment with polyunsaturated fatty acids," Journal of Japanese Opthalmological Society, 2003, 107: 199, see 130 (with English translation).
Zhang et al., "Epoxy metabolites of docosahexaenoic acid (DHA) inhibit angiogenesis, tumor growth, and metastasis," PNAS, 2013, 110(16):6530-6535.
Agbor et al., "Elevated blood pressure in cytochrome P4501A1 knockout mice is associated with reduced vasodilation to omega-3 polyunsaturated fatty acids," Toxicology and Applied Pharmacology, 2012, 264: 351-360.
Jung et al., "Effect of cytochrome P450-dependent epoxyeicosanoids on Ristocetin-induced thrombocyte aggregation," Clinical Hemorheology and Microcirculation, 2012, 52: 403-416.
Office Action in Australian Application No. 2014205369, dated Jul. 3, 2018, 3 pages.
Office Action in European Application No. 14737722.0, dated Feb. 14, 2018, 7 pages.
Office Action in Japanese Application No. 2015-552772, dated Jul. 24, 2018, 7 pages (with English translation).

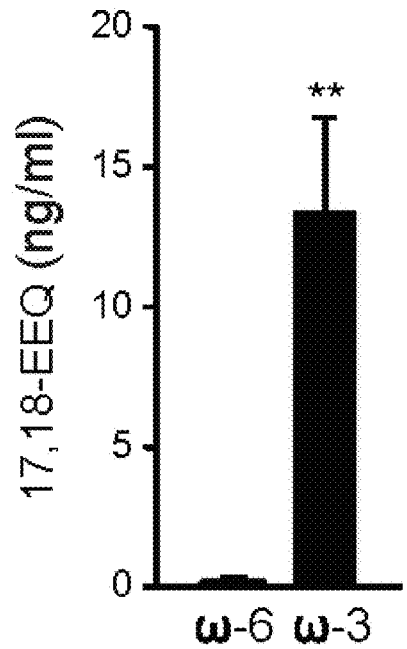
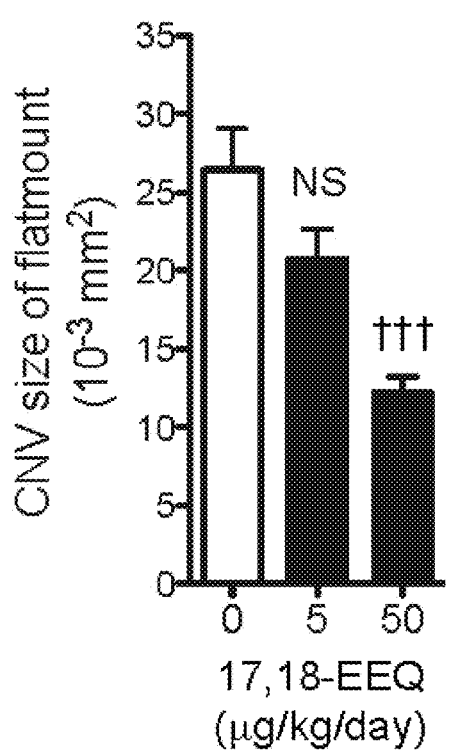
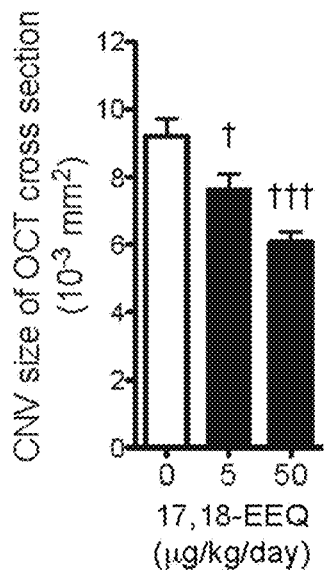
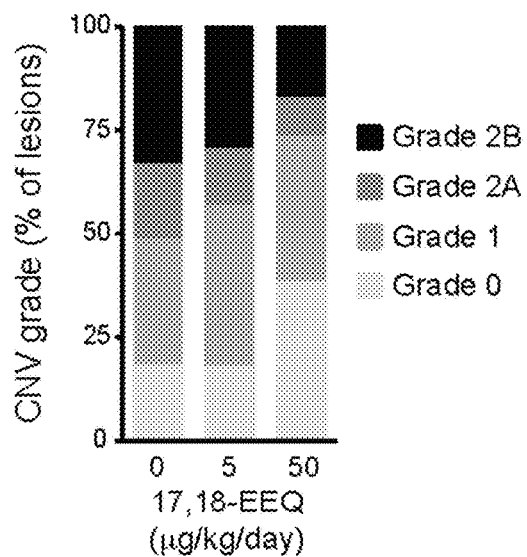
FIG. 3A
FIG. 3B
FIG. 3C
FIG. 3D

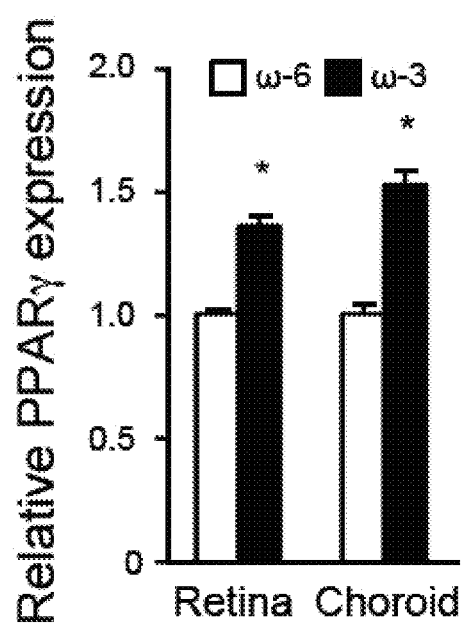 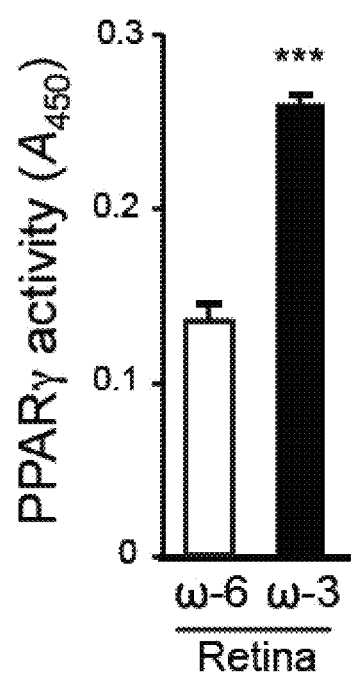
FIG. 4C
FIG. 4D

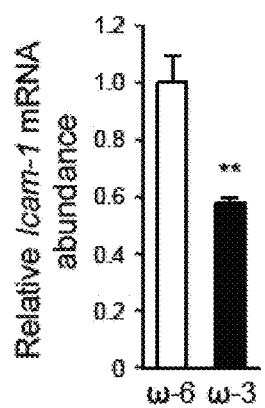 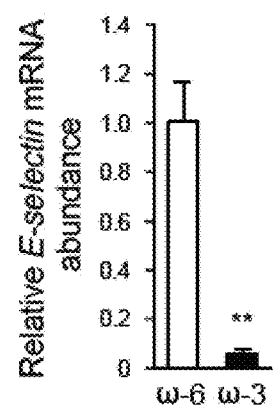
FIG. 5B  FIG. 5C
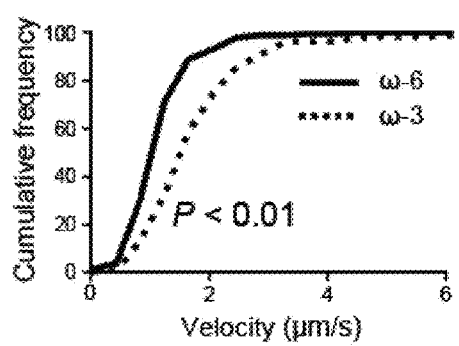 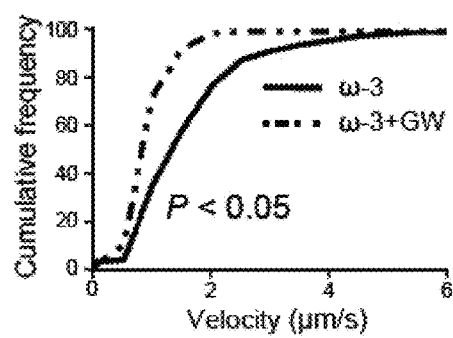
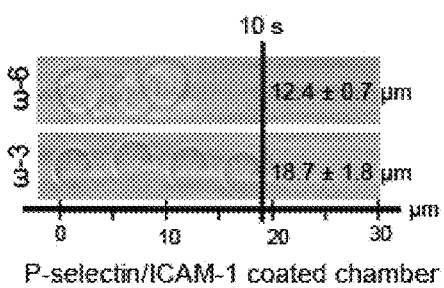 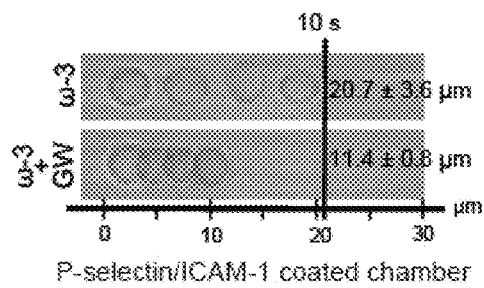
FIG. 5D  FIG. 5E

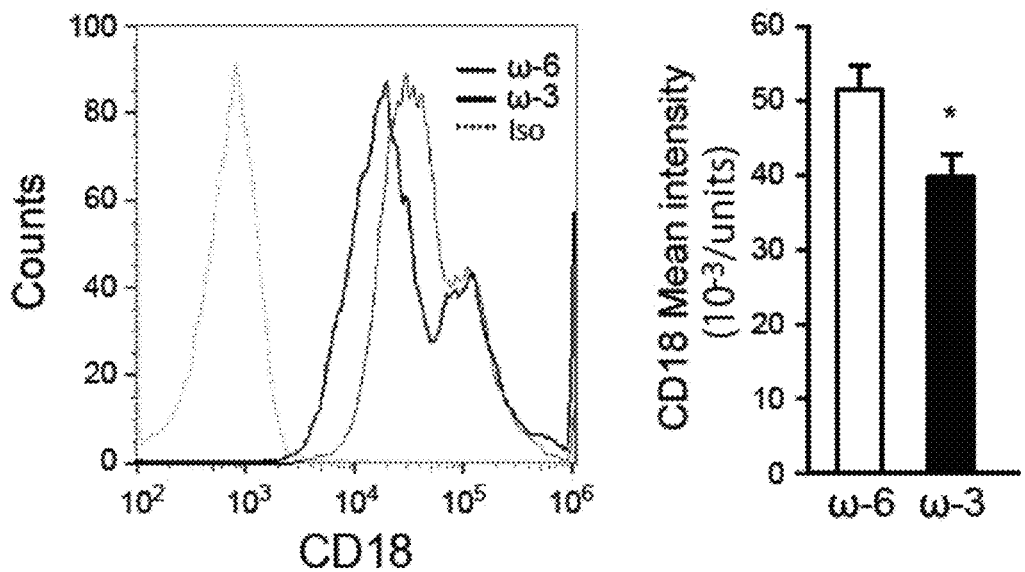
FIG. 5H
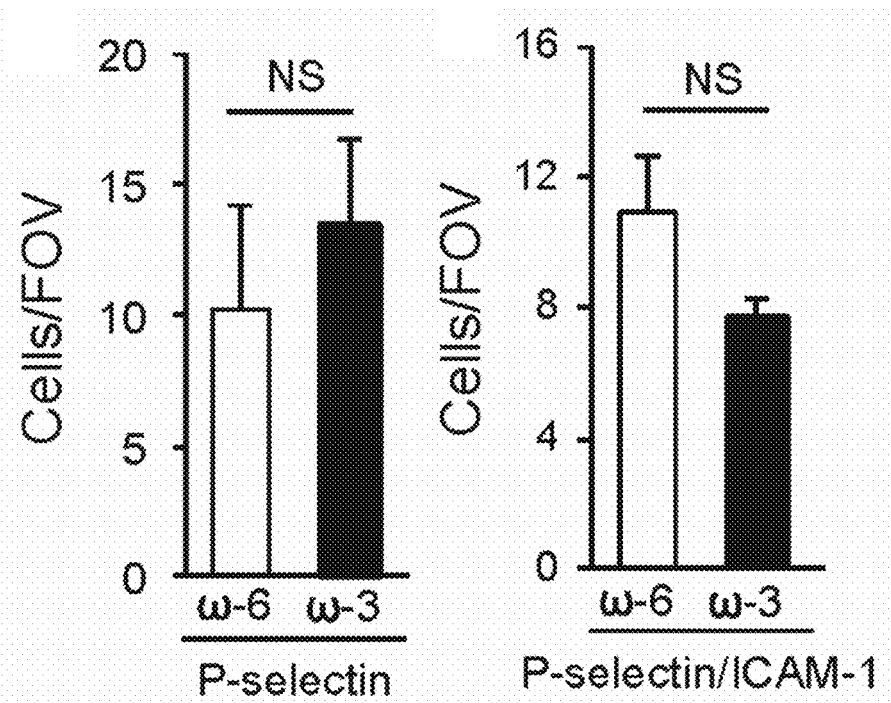
FIG. 5I
FIG. 5J

FIG. 9A
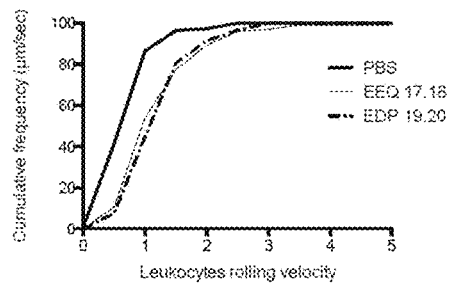
FIG. 9B
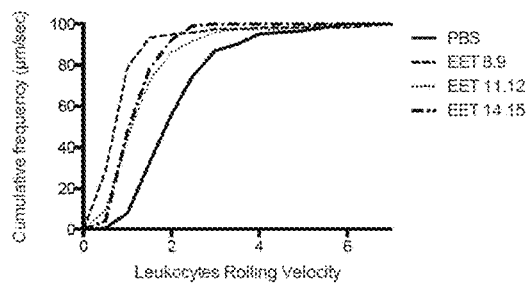
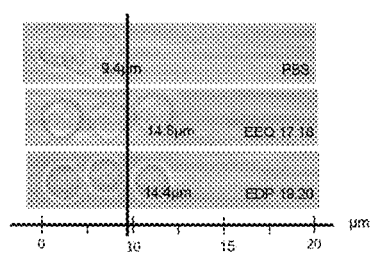
FIG. 9C
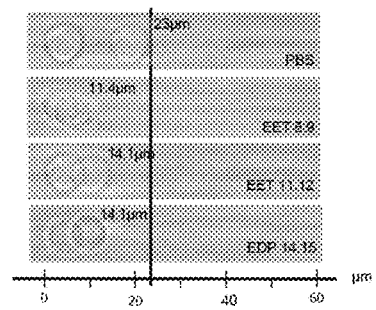
FIG. 9D
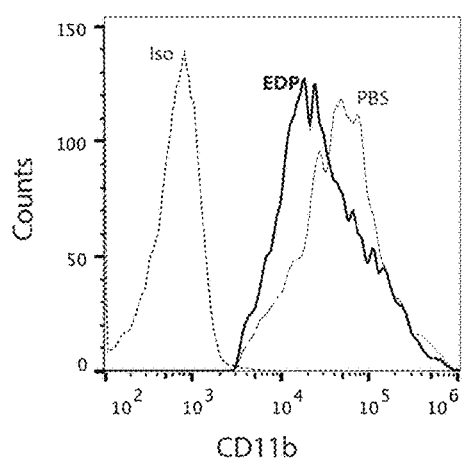
FIG. 9E
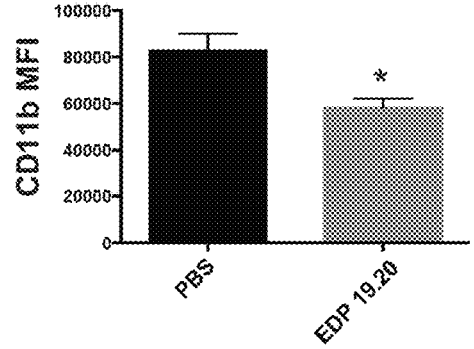
FIG. 9F

CYP450 LIPID METABOLITES REDUCE INFLAMMATION AND ANGIOGENESIS

CLAIM OF PRIORITY

This application is a continuation application of U.S. patent application Ser. No. 14/758,724, filed on Jun. 30, 2015, which is the U.S. National Stage of PCT/US2014/010880, filed on Jan. 9, 2014, which claims the benefit of U.S. Provisional Patent Application Ser. No. 61/751,617, filed on Jan. 11, 2013. The entire contents of the foregoing are hereby incorporated by reference.

FEDERALLY SPONSORED RESEARCH OR DEVELOPMENT

This invention was made with Government support under Grant Nos. R01EY022084-01/S1, T32EY007145 and P30EY014104 awarded by the National Institutes of Health. The Government has certain rights in the invention.

TECHNICAL FIELD

This invention relates to methods for reducing inflammation and angiogenesis, e.g., reducing or reversing angiogenesis, in a subject by administering a pharmaceutical composition comprising one or more epoxymetabolites derived from omega-3 long chain polyunsaturated fatty acids (ω-3 LCPUFAs), e.g., cytochrome P450 (CYP) derived epoxymetabolites of docosahexaenoic acid (DHA), including epoxydocosapentaenoic acid (EDP) analogs (e.g., 7,8-EDP; 10,11-EDP; 13,14-EDP; 16,17-EDP; 19,20-EDP); and/or CYP-derived epoxymetabolites of eicosapentaenoic acid (EPA) including epoxyeicosaquatraenoic acid (EEQ) analogs (e.g., 8,9-EEQ; 11,12-EEQ; 14,15-EEQ; 17,18-EEQ), e.g., one or both of 17,18-epoxyeicosatetraenoic acid (EEQ) and 19,20-epoxydocosapentaenoic acid (EDP), optionally with a pharmaceutically acceptable carrier. The methods can be used for the treatment of conditions associated with inflammation and/or excess angiogenesis or neovascularization, including ophthalmological conditions such as age-related macular degeneration, diabetic retinopathy and cancer; conditions associated with increased vascular permeability, including stroke and cancer, and conditions associated with inflammation, e.g., arthritis.

BACKGROUND

Age-related macular degeneration (AMD) is the primary cause of blindness in elderly individuals of industrialized countries,[1,2] and has a projected 50% increase by the year 2020.[3] There is an urgent need for new nutritional or pharmacological interventions that are safe over the long term for the treatment or prevention of AMD.

SUMMARY

At least in part, the present invention is based on the discovery that bioactive lipid metabolites derived from ω-3 LCPUFAs are effective in reducing inflammation, in causing neovessel regression, and in reducing vascular leakage.

Thus, in a first aspect, the invention provides methods for treating or reducing risk of a disorder associated with neovascularization in a subject. The methods include administering a therapeutically effective amount of a pharmaceutical composition comprising one or more epoxymetabolites of Docosahexaenoic acid (DHA) and Eicosapentaenoic acid (EPA), e.g., as listed in Table A, e.g., 17,18-EEQ and/or 19,20-EDP, and a pharmaceutically acceptable carrier. In some embodiments, the composition comprises 17,18-EEQ and/or 19,20-EDP, e.g., substantially purified 17,18-EEQ and/or 19,20-EDP. In some embodiments, the composition consists substantially of, or consists of as the sole active ingredients, one or more epoxymetabolites of Docosahexaenoic acid (DHA) and Eicosapentaenoic acid (EPA), e.g., as listed in Table A, e.g., 17,18-EEQ and/or 19,20-EDP, e.g., does not include any other active ingredients.

In some embodiments, the disorder is an ophthalmological disorder associated with neovascularization, e.g., associated with corneal, retinal, choroidal, uveal, or iris neovascularization. In some embodiments, the ophthalmological disorder associated with neovascularization is age-related macular degeneration, e.g., neovascular AMD, or atrophic AMD, and the treatment results in blood vessel regression. In some embodiments, the ophthalmological disorder associated with neovascularization is retinopathy or Stargardt's disease. In some embodiments, the retinopathy is selected from a group comprising of: retinopathy of prematurity (ROP); diabetic retinopathy; retinal vein occlusion; sickle cell retinopathy; and radiation retinopathy. In some embodiments, the administering is topical or parenteral administration into the eye. In some embodiments, administration is by local injection into or near the cornea, retina, vitreous, uvea, orbit, eyelid, conjunctiva, or iris.

In some embodiments, the disorder is cancer.

In another aspect, the invention provides methods for treating or reducing risk of a disorder associated with inflammation in a subject. The methods include administering a therapeutically effective amount of a pharmaceutical composition comprising one or more epoxymetabolites of ω-3 LCPUFAs, e.g., as listed in Table A, e.g., 17,18-EEQ and/or 19,20-EDP, and a pharmaceutically acceptable carrier. In some embodiments, the composition comprises 17,18-EEQ and/or 19,20-EDP, e.g., substantially purified 17,18-EEQ and/or 19,20-EDP. In some embodiments, the disorder is arthritis.

In yet another aspect, the invention provides methods for treating or reducing risk of a disorder associated with vascular leakage in a subject. The methods include administering a therapeutically effective amount of a pharmaceutical composition comprising one or more epoxymetabolites of ω-3 LCPUFAs, e.g., as listed in Table A, e.g., 17,18-EEQ and/or 19,20-EDP, and a pharmaceutically acceptable carrier. In some embodiments, the disorder is stroke.

In additional aspect, the invention provides the use of an epoxymetabolite of Docosahexaenoic acid (DHA) and Eicosapentaenoic acid (EPA), e.g., as listed in Table A, e.g., 17,18-EEQ and/or 19,20-EDP, for treating a disorder associated with neovascularization in a subject; for treating a disorder associated with neovascularization in a subject; and for treating a disorder associated with neovascularization in a subject. In some embodiments, the composition comprises 17,18-EEQ and/or 19,20-EDP, e.g., substantially purified 17,18-EEQ and/or 19,20-EDP.

In some embodiments, the disorder is an ophthalmological disorder associated with neovascularization, e.g., associated with corneal, retinal, choroidal, uveal, or iris neovascularization. In some embodiments, the ophthalmological disorder associated with neovascularization is age-related macular degeneration, e.g., neovascular AMD, or atrophic AMD, and the treatment results in blood vessel regression. In some embodiments, the ophthalmological disorder associated with neovascularization is retinopathy or Stargardt's disease. In some embodiments, the retinopathy is selected from a group comprising of: retinopathy of prematurity (ROP); diabetic retinopathy; retinal vein occlusion; sickle cell retinopathy; and radiation retinopathy. In some embodiments, the administering is topical or parenteral administration into the eye. In some embodiments, administration is by local injection into or near the cornea, retina, vitreous, uvea, orbit, eyelid, conjunctiva, or iris.

In some embodiments, the disorder is cancer, stroke, or arthritis.

In the present methods, "administering" epoxymetabolites of omega-3 long chain polyunsaturated fatty acids (ω-3 LCPUFAs), e.g., as listed in Table A, e.g., one or both of 17,18-epoxyeicosatetraenoic acid (EEQ) and 19,20-epoxydocosapentaenoic acid (EDP), means delivering to the subject the epoxymetabolite(s) themselves, and does not include in vivo conversion of ω-3 LCPUFAs to the epoxymetabolites in the subject. In some embodiments, the compounds are substantially purified, e.g., are at least 20% pure, and so the methods can include administering a pharmaceutical composition that is at least 20%, 30%, 40%, 50%, 60%, 70%, 70%, 80%, or 90% pure weight/weight of total active compounds.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 3A-H. ω-3 derived CYP-eicosanoids suppresses laser-induced CNV. Intraperitoneal injection with 17,18-EEQ, or 19,20-EDP were given on a daily basis, beginning immediately after CNV induction in mice fed with normal Purina chow. (A and E) Serum concentrations of 17,18-DHEQ +EEQ (A) and 19,20-DHDP +EDP (E) as determined by LC-MS/MS at 7-days after CNV induction in mice fed a diet enriched in ω-6 or ω-3-LCPUFAs. Data are means±SEM (n=8). $P<0.01$, *$P<0.001$. (B and F, top) Lesion size at 7-days after CNV induction as determined by staining of choroidal flatmount preparations with fluorescent isolectin B4 for mice fed a normal diet and injected intraperitoneally with (B) vehicle (n=27) or 17,18-EEQ at 5 (n=27) or 50 (n=26) μg/kg/day; or with (F) vehicle (n=30) or 19,20-EDP at 5 (n=26) or 50 (n=25) μg/kg/day. Data are means±SEM †††$P<0.001$; NS, not significant versus corresponding value for mice injected with vehicle. Representative staining of CNV lesions quantified in above (bottom panels). Scale bar, 50 μm. (C and G, top) Cross-sectional area of lesions quantified by SD-OCT at 7-days after CNV induction in mice fed a normal diet and injected with (C) vehicle (n=52) or 17,18-EEQ at 5 (n=58) or 50 (n=50) μg/kg/day; or with (G) vehicle (n=57) or 19,20-EDP at 5 (n=57) or 50 (n=58) μg/kg/day. Data are means±SEM †$P<0.05$, †††$P<0.001$ versus corresponding value for mice injected with vehicle. Representative SD-OCT images of CNV lesions (demarcated by red dashed lines) quantified in above (bottom panels). Scale bars, 50 μm. (D and H, top) Fluorescein angiography of lesions at 7-days after CNV induction in mice fed a normal diet and injected intraperitoneally with (D) vehicle (n=76) or 17,18-EEQ at 5 (n=72) or 50 (n=65) μg/kg/day or with (H) vehicle (n=76) or 19,20-EDP at 5 (n=73) or 50 (n=64) μg/kg/day. Representative fluorescein angiographic images quantified in above (bottom panels).

FIGS. 4A-H. Upregulation of PPARγ expression and activity in laser-induced CNV with dietary ω-3 LCPUFAs. (A) Real-time PCR analysis of Pparγ mRNA in the retina and choroid at 7-days after the induction of CNV in mice fed ω-6 or ω-3 LCPUFAs. Data are means±SEM (n=3). *$P<0.05$. (B) Immunoblot analysis of PPARγ in the retina and choroid at 7-days after CNV induction in mice fed ω-6 or ω-3 LCPUFAs. (C) Quantitation of PPARγ in immunoblots (n=6) similar to those in (B). Data are normalized by the abundance of β-actin (loading control) and are means±SEM *$P<0.05$. (D) PPARγ activity in nuclear extracts of the retina at 7-days after CNV induction in mice fed ω-6 or ω-3 LCPUFAs was determined with an enzyme-linked immunosorbent assay (ELISA). Data are expressed as absorbance at 450 nm ($A_{450}$) and are means±SEM (n=6). ***$P<0.001$. (E-G) Mice were given either a high ω-3 LCPUFAs or a high ω-6 LCPUFAs diet two weeks prior to laser-induced CNV. (E) Lesion size at 7-days after CNV induction in mice with ω-3 LCPUFAs intervention and injection of either PPARγ-inhibitor GW9662 or vehicle (n=50 and 50 lesions, respectively), and in vehicle-injected mice on ω-6 LCPUFAs served as controls (n=73) from CNV induction was assessed by staining of choroidal flat-mount preparations with fluorescent isolectin B4. Data are means±SEM ††P<0.01 versus corresponding value for mice on ω-6 LCPUFAs injected with vehicle. § P<0.05 versus corresponding value for mice on ω-3 LCPUFAs injected with vehicle. Representative staining of CNV lesions quantified in above (bottom panels). Scale bar, 50 μm. (F) Cross-sectional area of lesions quantified by SD-OCT at 7-days after CNV induction in mice with ω-3 LCPUFAs intervention and injection of either PPAR γ-inhibitor GW9662 or vehicle (n=36 and 56 lesions, respectively) or vehicle-injected mice on ω-6 LCPUFAs served as controls (n=69) from CNV induction. Data are means±SEM †††P<0.001 versus corresponding value for mice on ω-6 LCPUFAs injected with vehicle. §§§ P<0.001 versus corresponding value for mice on ω-3 LCPUFAs injected with vehicle. Representative SD-OCT images of CNV lesions (demarcated by red dashed lines) quantified in bottom. Scale bars, 50 μm. (G) Fluorescein angiography of lesions at 7-days after CNV induction in mice with ω-3 LCPUFAs intervention and injection of either PPARγ-inhibitor GW9662 or vehicle (n=56 and 56 lesions, respectively) or vehicle-injected mice on ω-6 LCPUFAs served as controls (n=80) from CNV induction. Lesions were graded on an ordinal scale based on the spatial and temporal evolution of fluorescein leakage. Representative fluorescein angiographic images quantified in bottom. (H) PPARγ activity in nuclear extracts of the retina at 7-days after CNV induction in mice with ω-3 LCPUFAs intervention and injection of either PPARγ-inhibitor GW9662 or vehicle, and in vehicle-injected mice on ω-6 LCPUFAs served as controls from CNV induction was determined with ELISA. Data are expressed as absorbance at 450 nm ($A_{450}$) and are means±SEM (n=6). †P<0.05 versus corresponding value for mice on ω-6 LCPUFAs injected with vehicle. §§§ P<0.001 versus corresponding value for mice on ω-3 LCPUFAs injected with vehicle. ‡P<0.05 versus corresponding value for mice on ω-6 LCPUFAs injected with vehicle.

FIGS. 5A-H. Down-regulation of adhesion molecules, quantitative analysis of leukocyte behavior under flow conditions and CD11b and CD18 expression on the cell surface for mice fed ω-6 or ω-3 LCPUFAs. (A) Representative isolectin B4 staining of a CNV lesion in a chorioretinal section. The red dashed line indicates the border of the sample isolated by laser-capture microdissection. Scale bar, 50 μm. (B and C) Real-time PCR analysis of Icam-1 (B), E-selectin (C) mRNAs in laser-captured CNV lesions at 7-days after CNV induction in mice fed ω-6 or ω-3 LCPUFAs. Data are means±SEM (n=3). **P<0.01,(D-F). Cumulative frequency of leukocyte rolling velocity a chamber coated with both P-selectin and ICAM-1 (D and E, top), or in a P-selectin-coated chamber (F, top) at 3-days after CNV induction in mice fed ω-6 (n=6 for D, n=7 for F) or ω-3 (n=6 for D, n=5 for F) LCPUFAs. Cumulative frequency of leukocyte rolling velocity a chamber coated with P-selectin and ICAM-1 (E, top) at 3-days after CNV induction in mice fed ω-3 LCPUFAs and injection of either PPARγ-inhibitor GW9662 (n=4) or vehicle (n=3). Representative overlay of individual leukocytes tracked over 10 seconds (D-F, bottom). (G and H, left) Flow cytometric analysis of CD11b (G) and CD18 (H) expression on PBLs at 3-days after CNV induction in mice fed ω-6 (n=6 and 3, respectively) or ω-3 (n=6 and 4, respectively) LCPUFAs. (G and H, right) Representative geometric mean fluorescence intensity values (means±SEM) are shown. *P<0.05.

FIGS. 5I-J. Quantitative analysis of leukocyte behavior under flow conditions for mice fed ω-6 or ω-3 LCPUFAs. (I and J) Number of interacting leukocytes per field of view (FOV) in chambers coated with P-selectin (I), or the combination of P-selectin and ICAM-1 (J). Data are means±SEM (n=10).

FIGS. 9A-D. The EEQ and EDP derived metabolites decrease recruitment to the lesion site by increasing rolling velocity in these animal. (A and C) EPA derived 17,18-EEQ and DHA derived 19,20-EDP metabolites decreased rolling. (B and D) AA-derived 8,9-EET, 11,12-EET, and 14,15-EET metabolites increased leucocyte rolling.

FIGS. 9E-L. CYP metabolites have differing effects on ICAM ligands. (E-H) EDP suppresses CD11b (E and F) but not CD18 (G and H) in peripheral blood leukocytes. (I-L) EEQ suppresses CD18 (K and L) but not CD11b (E and F) in peripheral blood leukocytes.

DETAILED DESCRIPTION

Figure 1A:
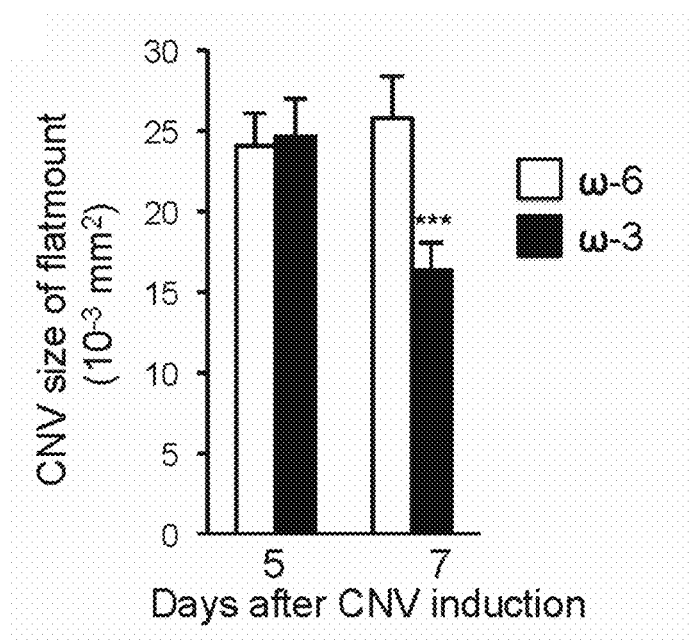
FIGs 1A-F. Dietary intake of ω-3 LCPUFAs attenuates CNV. A, Lesion size at 5 and 7 days after CNV induction, as assessed by staining of choroidal flat-mount preparations with fluorescent isolectin B4 in mice fed a diet enriched in ω-6 LCPUFAs (n=61 and 69 lesions, respectively) or in ω-3 LCPUFAs (n=63 and 65 lesions, respectively). Data are means±s.e.m. *$P<0.001$. B, Representative staining of CNV lesions quantified in A. Scale bar, 50 μm. C, Cross-sectional area of lesions quantified by SD-OCT at 5 and 7 days after CNV induction in mice fed an ω-6 LCPUFA diet (n=60 and 53 lesions, respectively) or an ω-3 LCPUFA diet (n=64 and 55 lesions, respectively). Data are means±s.e.m. *$P<0.001$. D, Representative SD-OCT images of CNV lesions (demarcated by red dashed lines) quantified in C. Scale bars, 50 μm. E, Fluorescein angiography of lesions at 5 and 7 days after CNV induction in mice fed an ω-6 LCPUFA diet (n=72 lesions, each day) or an ω-3 LCPUFA diet (n=96 and 80 lesions, respectively). Lesions were graded on an ordinal scale based on the spatial and temporal evolution of fluorescein leakage. F, Representative fluorescein angiographic images quantified in E.
Figure 1B:
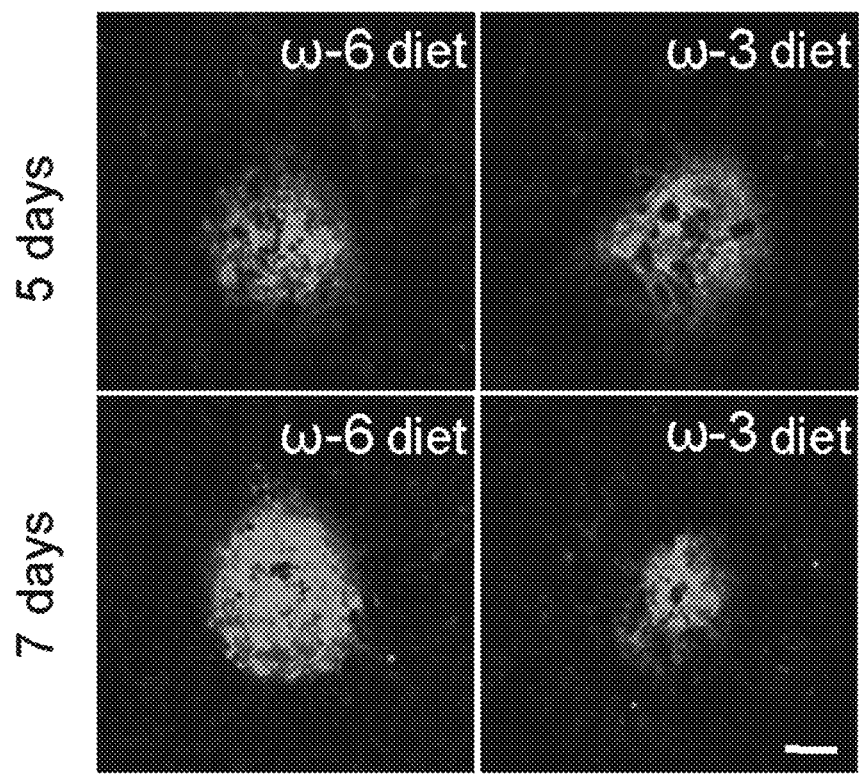

Prospective clinical studies have suggested that dietary intake of ω-3 long-chain polyunsaturated fatty acids (LCPUFAs) may have a protective effect against AMD.[4-7] As demonstrated herein, dietary supplementation of ω-3 LCPUFAs mediates resolution of choroidal neovessel in a well-characterized murine model of neovascular AMD. The serum lipid profiles in these mice are elevated in the anti-inflammatory eicosanoids docosahexaenoic acid (DHA) and eicosapentaenoic acid (EPA), the primary ω-3 LCPUFAs. The cytochrome P450 (CYP) enzymes catalyze the epoxidation of these ω-3 LCPUFAs to form the eicosanoids 17,18-epoxyeicosatetraenoic acid (EEQ) and 19,20-epoxy-docosapentaenoic acid (EDP), which were identified as key lipid mediators of disease resolution. Furthermore, by dampening systemic inflammation, ω-3 LCPUFAs suppress leukocyte recruitment to the disease site by down-regulating endothelial ICAM-1 and E-selectin as well as leukocyte CD11b and CD18 expression. Bioactive lipid metabolites derived from ω-3 LCPUFAs show promising therapeutic potential in AMD disease resolution.

Methods of Treatment

The methods described herein include methods for the treatment of disorders associated with inflammation and/or angiogenesis, e.g., neovascularization. In some embodiments, the disorder is associated with choroidal neovascularization (CNV), e.g., AMD. In some embodiments, the disorder is associated with tumor neovascularization, e.g., cancer, e.g., ocular cancer. In addition, the methods described herein include methods for the treatment of disorders associated with inflammation or "leaky" vasculature, e.g., stroke or arthritis. Generally, the methods include administering a therapeutically effective amount of epoxymetabolites of ω-3 LCPUFAs as described herein, e.g., as shown in Table A, to a subject who is in need of, or who has been determined to be in need of, such treatment. In some embodiments, the methods include administering a therapeutically effective amount of 17,18-EEQ or 19,20-EDP to a subject who is in need of, or who has been determined to be in need of, such treatment. Examples of routes of administration include parenteral, e.g., intravenous, intraperitoneal, intradermal, or subcutaneous; topical; and oral administration. In some embodiments, for treatment of ophthalmic conditions, intraocular administration or administration by eye drops may be used, inter alia.

In some embodiments, the disorder will stem from overformation of blood vessels, or formation of blood vessels in an unwanted area, e.g., in the avascular regions of the eye, e.g., retinopathies, or in a tumor, e.g., a cancerous or benign tumor. For example, the ophthalmological disorder can be age-related macular degeneration (AMD), where new blood vessels grow under the retina, or retinopathy, e.g., diabetic retinopathy, where abnormal vessels grow on top of the retina. Other ophthalmological disorders include retinopathy (e.g., selected from a group comprising of: retinopathy of prematurity (ROP); diabetic retinopathy; retina vein occlusion; sickle cell retinopathy; Stargardt's disease; choroidal neovascularization, radiation retinopathy), microangiopathy, neovascular glaucoma, corneal graft rejection, glaucoma, herpetic and infectious keratitis, ocular ischemia, neovascular glaucoma, corneal, uveal and iris neovascularization, orbital and eyelid tumors, Stevens Johnson Syndrome, ocular cicatricial pemphigoid, wounds or other injuries (e.g., chemical injuries due to exposure to irritants, acids or bases), and ocular surface diseases. The disorder can be characterized by, for example, surface, corneal, retinal, choroidal, uveal, or iris neovascularization.

The disorder may stem from the formation of blood vessels that deliver blood to a tissue, e.g., a primary or metastatic cancerous or benign tumors, e.g., cancer. A metastatic tumor can arise from a multitude of primary tumor types, including but not limited to those of prostate, colon, lung, breast and liver origin.

As used herein, the terms "cancer," "hyperproliferative," and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair; thus, the methods include administration of a compound identified by a method described herein to maintain avascularity during wound healing. In this embodiment, the disorder is typically a wound, including both accidental as well as intentional wounds (e.g., surgical wounds), including ophthalmological wounds and injuries (e.g., chemical injuries due to exposure to irritants, acids or bases).

In some embodiments, the disorder is a cancer of the eye, e.g., eyelid tumors, e.g., malignant eye lid tumors, benign eye lid tumors, basal cell carcinoma, squamous cell carcinoma, sebaceous cell carcinoma, and malignant melanoma; conjunctival tumors, e.g., pigmented conjunctival tumors, melanoma and primary acquired melanosis with atypia, squamous conjunctival neoplasia, conjunctival lymphoma, and Kaposi's Sarcoma; iris tumors, e.g., iris melanoma, iris pigment epithelial cyst, anterior uveal metastasis, and pearl cyst of the iris; infiltrative intraocular tumors, e.g., multiple myeloma, lymphoma, and leukemia; choroidal tumors, e. g., choroidal melanoma, choroidal metastasis, choroidal nevus, choroidal hemangioma, choroidal osteoma, and Nevus of Ota; retinal tumors, e.g., retinoblastoma, retinal pigment epithelial tumors, retinal pigment epithelial hypertrophy, von Hippel angioma; optic nerve tumors, e.g., melanocytoma, melanoma, meningioma, circumpapillary metastasis; orbital tumors, e.g., lymphangioma, cavernous hemangioma, meningioma, mucocele, rhabdomyosarcoma, orbital pseudotumor, adenoid cystic carcinoma, periocular hemangioma of childhood; cancers of the ocular adnexa, e.g., lacrimal gland carcinomas such as adenoid cystic carcinoma and mucoepidermal epithelioma; and metastatic ocular tumors, e.g., metastatic choroidal melanoma, and metastatic retinoblastoma.

In some embodiments, the disorder is associated with, e.g., vasoproliferative ocular tumours (e.g., neoplastic and benign retinal vascular tumors such as retinal capillary hemangioma, hemangioblastomas, cavernous hemangiomas, Racemose Hemangioma (Wyburn-Mason Syndrome), Retinal Vasoproliferative Tumors, and tumors associated with Von Hippel-Lindau (VHL) disease; or choroidal vascular tumors including circumscribed choroidal hemangiomas and diffuse choroidal hemangiomas). See, e.g., Turell and Singh, Middle East Afr J Ophthalmol. 2010 Jul.-Sep.; 17(3): 191-200.

As used in this context, to "treat" means to ameliorate at least one symptom associated with abnormal angiogenesis as well as reduce neovascularization. For the treatment of cancers and solid tumors, to "treat" includes inhibition of the growth of blood vessels resulting in a lack of nutrients for the tumors and/or cancer cells needed by the tumor for its growth. Tumors and growths will decrease in size and possibly disappear. Administration of a therapeutically effective amount of a composition for the treatment of arthritic conditions will result in decreased blood vessel formation in cartilage, specifically joints, resulting in increased mobility and flexibility in these regions. In ophthalmologic conditions, administration of a therapeutically effective amount of a composition described herein will reduce the formation of extraneous blood vessels in the retina, resulting in unobstructed vision. In the treatment of disorders such as cancer, administration of a therapeutically effective amount of a composition described herein will inhibit the growth and/or further formation of blood vessels, thereby inhibiting the formation of any lesions and/or tumors that arise.

In addition, when the disorder is stroke, a treatment can result in a decrease in local inflammation and vascular leakage. When the disorder is arthritis, a treatment can result in a decrease in local inflammation.

Age-Related Macular Degeneration

Advanced AMD is characterized as "atrophic" or "neovascular," the former showing loss of outer retinal layers, and the latter the presence of choroidal neovascularization (CNV).[8] Neovascular (or "wet") AMD is defined by the formation of abnormal blood vessels that grow from the choroidal vasculature, through breaks in Bruch's membrane, toward the outer retina[1]. These blood vessels are immature in nature and leak fluid below or within the retina.[9] The two forms of AMD can occur together and share pathologies of cell death and fibroglial replacement.[10,11] Neovascular AMD accounts for 10 to 15% of AMD cases, develops abruptly, and rapidly leads to substantial loss of vision.[9,12] Although growth factors appear to play an important role in the late stage of neovascular AMD progression, they likely do not contribute to the underlying cause of the disease. Current standard of care for patients with CNV involves targeting the proangiogenic and permeability molecule vascular endothelial growth factor-A (VEGF).[13-15] However, although anti-VEGF therapy blocks vascular permeability and angiogenesis, it does not lead to complete vascular regression.[14] Moreover, in patients treated with VEGF antagonists, substantial vision improvement occurs in only one-third, with one-sixth of treated patients still progressing to legal blindness.[13,15] Thus, there is an urgent need for safe nutritional or pharmacological interventions for the treatment and ideally the prevention of AMD.

Vascular Permeability

Figure 3E:
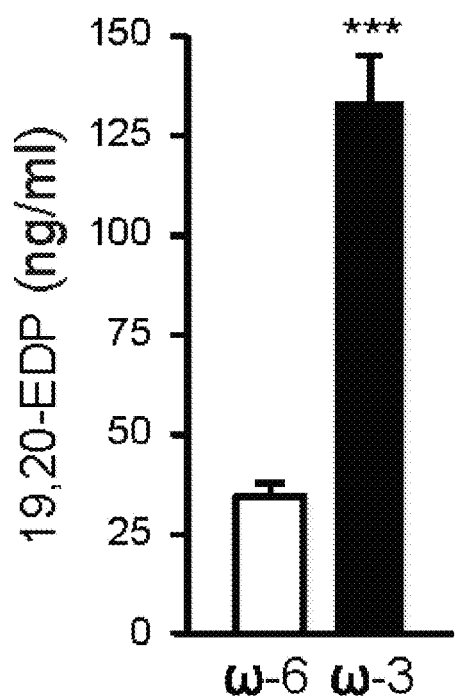
Figure 3F:
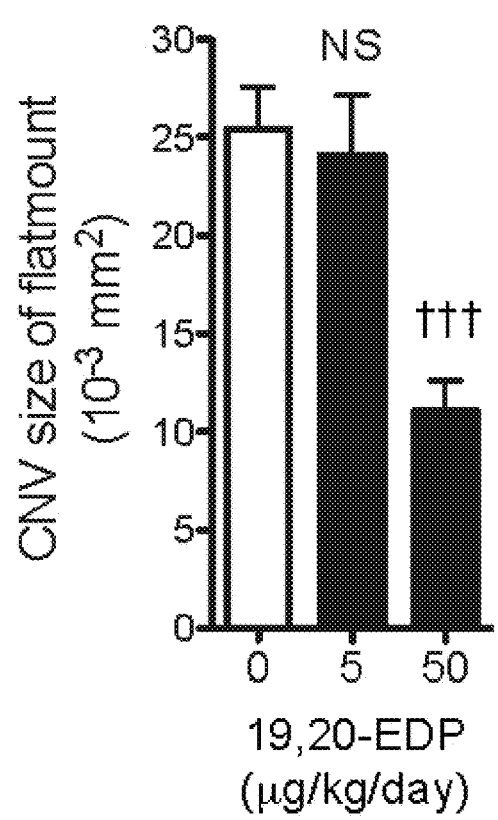
Figure 3G:
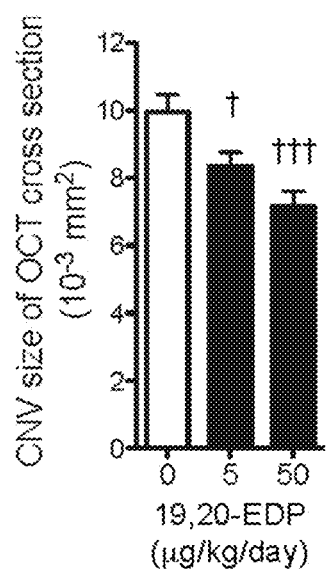
Figure 3H:
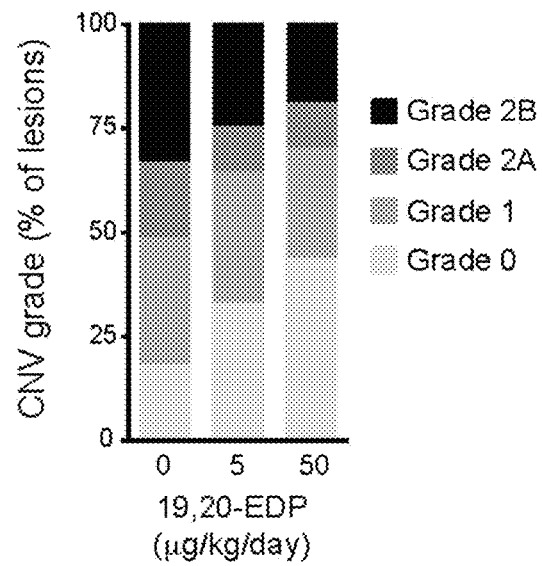

As shown in FIGS. 3D and 3H, the epoxymetabolites described herein reduce vascular permeability. The methods described herein can also be used to reduce vascular permeability, which has been shown to be associated with highly vascular cancers and stroke. The vascular leakage seen in these conditions has characteristics similar to those seen in the models described herein; see, e.g., Lee et al., Stroke. 2007;38:3289-3291; Lin et al., AJNR Aug. 2007 28: 1292-1298; Cao et al., Cancer Res Sep. 1, 2006 66; 8912.

Inflammation

As shown in FIGS. 9A-L, administration of the epoxymetabolites described herein reduces systemic leukocyte recruitment during CNV, and reduces inflammation. Thus, the methods described herein include the use of these compounds to treat conditions associated with inflammation, including arthritis, and to reduce systemic inflammation in a subject.

Epoxymetabolites of ω-3 LCPUFAs

The ω-3 and ω-6 LCPUFAs are two classes of dietary lipids that are highly enriched in the retina and have opposing physiological effects. The ω-3 LCPUFAs have anti-thrombotic and anti-inflammatory properties, and compete with ω-6 LCPUFAs for downstream eicosanoids synthesis at the CYP, cyclooxygenase, and lipoxygenase levels.[16] Mammals depend on dietary intake of LCPUFAs because they lack the enzymes that synthesize these molecules de novo. The ω-6 LCPUFAs are the primary polyunsaturated fatty acids found in western diets. Dietary enrichment with ω-3 LCPUFAs has been shown to be protective against pathological angiogenesis, which occurs in cancer and retinopathies.[16-22] Prospective clinical studies have suggested that dietary ω-3 LCPUFAs may protect against AMD.[4,5] In a prospective cohort study of 1837 participants at moderate-to-high risk of developing advanced AMD, those who reported the highest intake of ω-3 LCPUFAs (median of 0.11% of total energy intake) were 30% less likely than their peers to develop the condition over a 12-year period.[7]

The Nutritional AMD Treatment 2 (NAT2) specifically assessed DHA supplementation and its role in CNV disease development; in this double-masked, randomized, parallel, comparative trial, patients with neovascular AMD in one eye were given oral DHA or a placebo over three years and the study eye was assessed for time of occurrence of CNV (Souied et al., OPHTHA, 120(8):1619-1631 (2013). It was observed that in patients with high EPA plus DHA levels there was a significant decrease in CNV development over the three years (-68%). These data indicates that these molecules have potent anti-angiogenic properties. Given that retinal LCPUFA tissue status is dependent on dietary intake, and that ω-3 LCPUFA intake is relatively low in Western diets, the present inventors hypothesized that these nutrients are reasonable therapeutic interventions for neovascular AMD.

Interestingly, the NIH-initiated Age-Related Eye Disease Study 2 (AREDS2) found no protective effects from dietary supplementation with ω-3 LCPUFAs on disease progression (both GA and CNV) (The Age-Related Eye Disease Study 2 (AREDS2) Research Group/Chew et al., JAMA: the Journal of the American Medical Association, 309(19):2005-2015 (2013). In AREDS2, the dose of supplemented DHA (the primary ω-3 in the retina) was significantly lower than the in NAT2 study (Souied et al., (2013)), suggesting that supplementation dose is crucial to CNV outcome. Moreover, the placebo group in AREDS2 was not a true placebo, as it was also supplemented with the AREDS1 formulation. Lastly, in AREDS2, GA and CNV were used as diagnostic markers of disease progression; the effect of these lipids on CNV was not directly studied.45 Of note, patients in the NAT2 study also still progressed with GA independent of supplementation (Souied et al., (2013)). Patients in the NAT2 with highest systemic levels of DHA/EPA had a significant decrease (68%) in progression to CNV (Souied et al., (2013)). This interesting finding supports the notion that these dietary lipids do indeed affect the vasculature.

The present disclosure elucidates a pathway by which dietary intake of ω-3 LCPUFAs facilitates choroidal neovessel resolution in a mouse model of laser-induced CNV, and demonstrates that administration of epoxymetabolites of ω-3 LCPUFAs is useful in treating neovascularization characteristic of AMD.

The methods described herein include administering a composition comprising one or more epoxymetabolites of omega-3 long chain polyunsaturated fatty acids (ω-3 LCPUFAs), e.g., as listed in Table A, e.g., one or both of 17,18-epoxyeicosatetraenoic acid (EEQ) and 19,20-epoxydocosapentaenoic acid (EDP). In preferred embodiments, the compounds are synthesized ex vivo, e.g., biosynthesized using recombinant CYP450 from DHA or EPA. See, e.g., Lucas et al., J Lipid Res. 2010 May; 51(5): 1125-1133.

TABLE A

Cytochrome P450 (CYP) Derived Epoxymetabolites of Docosahexaenoic acid (DHA) and Eicosapentaenoic acid (EPA)

| Analogs of | Derived from | Name |
|---|---|---|
| epoxydocosapentaenoic acid (EDP) | Docosahexaenoic acid (DHA) | 4,5-EDP |
| | | 7,8-EDP |
| | | 10,11-EDP |
| | | 13,14-EDP |
| | | 16,17-EDP |
| | | 19,20-EDP |
| epoxyeicosaquatraenoic acid (EEQ) | Eicosapentaenoic acid (EPA) | 5,6-EEQ |
| | | 8,9-EEQ |
| | | 11,12-EEQ |
| | | 14,15-EEQ |
| | | 17,18-EEQ |

Pharmaceutical Compositions

The methods described herein can include the use of pharmaceutical compositions comprising one or more epoxymetabolites of ω-3 LCPUFAs, e.g., as listed in Table A, preferably 17,18-EEQ and/or 19,20-EDP. Such compositions typically include the active ingredient and a pharmaceutically acceptable carrier. As used herein the language "pharmaceutically acceptable carrier" includes diluents such as saline, solvents, dispersion media, coatings, antibacterial and antifungal agents, isotonic and absorption delaying agents, and the like, compatible with pharmaceutical administration. Supplementary active compounds can also be incorporated into the compositions, e.g., one or more anti-VEGF agents.

A pharmaceutical composition is typically formulated to be compatible with its intended route of administration. Examples of routes of administration include parenteral, e.g., intravenous, intraperitoneal, intradermal, subcutaneous, oral (e.g., inhalation), transdermal or topical, transmucosal, and rectal administration. For treatment of ophthalmic conditions, intraocular administration or eye drops may be used; see, e.g., U.S. Pat. No. 7,582,785. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.), liposomes or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer. Such methods include those described in U.S. Pat. No. 6,468,798.

Administration of a polypeptide or nucleic acid compound described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In some embodiments, the compositions are prepared with carriers that will protect the active ingredient against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially, e.g., from Alza Corporation or Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Dosage, toxicity and therapeutic efficacy of the compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. See, e.g., Shearer et al., J Lipid Res. 2010 August; 51(8):2074-81.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments. In some embodiments, a therapeutically effective amount, when administered systemically, is a dose sufficient to result in plasma concentrations of at least 150 nM for 17, 18-EEQ or 400 nM for 19,20-EDP. Exemplary doses include about 50 ng/day of each epoxymetabolite, e.g., at least 5 µg kg$^{-1}$ day$^{-1}$, 25 µg kg$^{-1}$ day$^{-1}$, 50 µg kg$^{-1}$ day$^{-1}$, e.g., 75 µg kg$^{-1}$ day$^{-1}$, 100 µg kg$^{-1}$ day$^{-1}$, 120 µg kg$^{-1}$ day$^{-1}$, 125 µg kg$^{-1}$ day$^{-1}$, 150 µg kg$^{-1}$ day$^{-1}$, 200 µg kg$^{-1}$ day$^{-1}$, 250 µg kg$^{-1}$ day$^{-1}$, 500 µg kg$^{-1}$ day$^{-1}$, or more, of each epoxymetabolite, e.g., of each of 17,18-EEQ and/or 19,20-EDP.

The pharmaceutical compositions can be included in a container, pack, or dispenser together with instructions for administration.

Combination Treatments—Anti-VEGF Agents

In some embodiments, the methods include co-administering an anti-Vascular Endothelial Growth Factor (VEGF) agent. In some embodiments, the anti-VEGF agent blocks VEGF signaling. There are at least three methods to block VEGF signaling that have been used to date. The first method is to inhibit VEGF (e.g. VEGF-A, -B, -C, -D, PGF) and/or VEGFR (e.g. VEGFR-1, -2, -3) using antibodies. Examples include: Avastin (bevacizumab), a recombinant humanized monoclonal antibody that binds to VEGF-A and prevent interaction of VEGF-A to VEGFR-1 and VEGFR-2 (see, e.g., Presta et al., Cancer Res. 57: 4593-4599 (1997); Hurwitz et al., N. Engl. J. Med. 350:2335-2342) (2004); 2C3, a mouse monoclonal antibody against VEGF-A (Zhang et al., Angiogenesis. 5:35-44 (2002); Brekken et al., Cancer Res. 58: 1952-9 (1998)); IMC-1121B, a human monoclonal antibody against VEGFR-2 (Rockwell and Goldstein, U.S. Pat. No. 6,811,779); CDP-791, PEGylated, humanized di-Fab fragment that binds to VEGFR-2 (Ton et al., Clin. Cancer Res. 13:7113-711 (2007)). Lucentis (ranibizumab) is a recombinant humanized monoclonal antibody that binds to VEGF-A, but its approved usage is for treatment of patients with neovascular age-related macular degeneration (available from Genentech).

A second method uses protein kinase inhibitors to inhibit VEGFR (e.g. VEGFR-1, -2, -3). At least two known FDA-approved small molecule inhibitors are on the market: Sutent (sunitinib) (Goodman et al., Clin. Cancer Res.

13:1367-1373 (2007)) and Nexavar (sorafenib) (Kane et al., Clin. Cancer Res. 12:7271-8 (2006)). Other kinase inhibitors include, but are not limited to: Vatalanib (PTK787/ZK222584) which inhibits VEGFR-1, -2, and -3 (Wood et al., Cancer Res. 60:2178-2189 (2000)); CEP-7055, inhibitor of VEGFR-1, -2, and -3 (Ruggeri et al., Cancer Res. 63: 5978-5991 (2003)); CP-547,632, inhibitor of VEGFR-2 and FGF (Beebe et al., Cancer Res. 63: 7301-7309 (2003)).

A third method uses the so-called "VEGF-trap," i.e., soluble hybrid VEGF receptors that bind to the VEGF ligand and prevent binding to VEGFRs (Holash et al., Proc. Natl. Acad. Sci. 99:11393-11398 (2002)).

In some embodiments, the anti-VEGF agent is an anti-VEGF antibody or antigen-binding portions thereof (such as Fv, Fab, or scFv portions) to inhibit VEGF binding to KDR and/or flt receptors, e.g., Avastin® (Bevacizumab). Avastin is a recombinant humanized monoclonal IgG1 antibody that binds to and inhibits the biologic activity of human VEGF both in vitro and in vivo. Bevacizumab contains human framework regions and the complementarity-determining regions of a murine antibody that binds to VEGF (Presta et al., Cancer Res 57:4593-9 1997). Avastin is available from Genentech (South San Francisco, Calif.). See also: Schlaeppi and Wood, Cancer and Metastasis Rev. 1999; 18:473-481; U.S. Pat. Nos. 7,169,901; 7,056,509; and U.S. Pat. No. 7,297,334; U.S. Pat. Pub. No. 20020032315; 20080187966; and 20090010883; and PCT No. WO 94/10202. In some embodiments, the antibody binds specifically to VEGF and block binding to VEGFR1, to VEGFR2, or block binding to both VEGFR1 and VEGFR2.

Other anti-VEGF agents include VEGF antagonists, which could compete with VEGF for binding to KDR and/or flt receptors (e.g. soluble truncated forms of flt receptor, which bind to VEGF, as described, for example, in WO 94/21679); and tyrosine kinase inhibitors.

In some embodiments, the anti-VEGF agent is a small interfering RNA (siRNA) targeting VEGF or a VEGFR, e.g., Bevasiranib (Cand5; OPKO Health; a modified siRNA targeting all VEGF-A splice forms) or AGN-745 (Sirna-027; Merck; a chemically modified siRNA targeting VEGFR-1), see, e.g., de Fougerolles, Human Gene Therapy 19:125-132 (2008); and anti-VEGF aptamers (e.g., Macugen (pegaptanib; OSI Pharmaceuticals, a pegylated anti-VEGF-A aptamer), see, e.g., Tremolada et al. Am. J. Cardiovasc. Drugs 7:393-398 (2007)).

In some embodiments, the anti-VEGF agent is administered as part of the same treatment regimen as the compounds described herein. In some embodiments, the anti-VEGF agent is co-administered, e.g., as part of the same pharmaceutical composition as described above.

EXAMPLES

The invention is further described in the following examples, which do not limit the scope of the invention described in the claims.

Materials and Methods

The following methods were used in Examples 1-9, below.

Mice. The present studies adhered to the Statement for the Use of Animals in Ophthalmic and Vision Research of the Association for Research in Vision and Ophthalmology and were approved by the Animal Care Committee of the Massachusetts Eye & Ear Infirmary. Male C57BL/6 mice (stock no. 000664) at 6 weeks of age were obtained from The Jackson Laboratory. Cx3cr1$^{GFP/+}$ mice (stock no. 005582), which express green fluorescent protein (GFP) specifically in monocytes, dendritic cells and microglia, were obtained from The Jackson Laboratory and were administered the same diets as C57BL/6 mice.

The animals were fed a defined rodent diet with 10% (w/w) safflower oil containing either 2% ω-6 LCPUFA (AA) with no ω-3 LCPUFAs or 2% ω-3 LCPUFAs (1% DHA and 1% EPA, with no AA) with no ω-6 LCPUFAs as previously described.[17] These diets were given 2 weeks prior to laser CNV induction. Given that the typical intake of ω-3 LCPUFAs in the United States (100 to 200 mg/day) provides ~0.05 to 0.1% of total calories, the amount of these fatty acids in the experimental diet is physiological and attainable by patients.

Dietary LCPUFAs were obtained from DSM Nutritional Products under the trade name ROPUFA, ARASCO and DHASCO. The feed was produced by Research Diets Inc. CX3CR1-GFP mice (stock no. 005582), which express GFP specifically in monocytes, dendritic cells and microglia, were obtained from The Jackson Laboratory and were administered the same diets as C57BL/6 mice.

Figure 2A:
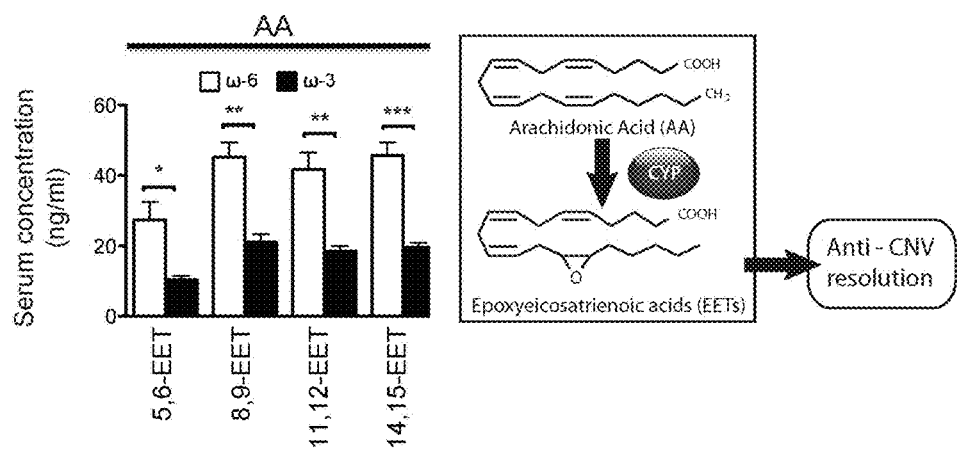
FIGS. 2A-C. Effects of dietary intake of ω-3 LCPUFAs on the profile of monoepoxides in serum. (A-C) Fatty acid profiles derived from AA (A), EPA (B), and DHA (C) were determined for serum (n=8) at 7-days after CNV induction in mice fed a diet enriched in ω-6 or ω-3 LCPUFAs. Data are means±SEM *$P<0.05$, $P<0.01$, *$P<0.001$. (left panels) Schematic presentation of genetic and pharmacological tools used to operate CNV resolution. Abbreviations: DHET, dihydroxy eicosatrienoic acids; EET, epoxy eicosatrienoic acid; DHEQ, dihydroxy eicosaquatraenoic acid; EEQ, epoxy eicosatetraenoic acid; DHDP, dihydroxy docosapentaenoic acid; EDP, epoxy docosapentaenoic acid. All quantitative data are means±SEM.

17,18-EEQ and 19,20-EDP were obtained from Cayman Chemical. Mice were injected intraperitoneally with 17,18-EEQ, 19,20-EDP, or phosphate-buffered saline (PBS) as a vehicle control daily beginning immediately after CNV induction. The dose was calculated from serum concentrations of 19,20-EHDP+EDP in mice fed ω-3 LCPUFAs (FIG. 2C) as an essential minimum steady-state level of CYP metabolites (5 µg/kg/day) for resolution of CNV and estimated 7% of body weight (23-25 g) as a circulating blood volume.

GW9662, a specific PPARγ-antagonist with a nanomolar inhibiter was injected IP daily on ω-3 LCPUFAs diets beginning immediately after CNV induction (1 mg/kg in 20 µL). Vehicle control was PBS/DMSO 1:1.

Laser-induced model of CNV. Laser photocoagulation was performed 2 weeks after the onset of feeding with the ω-3 or ω-6 LCPUFA diets with the use of a 532-nm laser (Oculight GLx Laser System, IRIDEX) attached to a slit-lamp, with a coverslip being used to applanate the cornea in order to afford a view of the posterior pole of the eye. Four lesions located at the 3, 6, 9, and 12 o'clock meridians centered on the optic nerve (size and leakage studies) or 10 lesions (protein and mRNA analysis) were induced in both eyes with the same settings: spot size of 100 µm, pulse duration of 0.1 s, and laser power of 100 mW.[25] The lesions were located two or three disc diameters from the optic nerve. Laser-induced disruption of Bruch's membrane was identified by the appearance of a bubble at the site of photocoagulation. Laser spots that did not result in the formation of a bubble were excluded from the studies. One investigator executed all laser photocoagulation.

Choroid flat-mount preparation. For evaluation of the size of CNV lesions, mice were anesthetized with Avertin (Sigma) and sacrificed by cervical dislocation at 5 or 7 days after laser photocoagulation. The eyes were removed and fixed in 4% paraformaldehyde for 60 min at room temperature, the cornea and lens were removed, and the entire retina was carefully dissected from the eyecup. Radial cuts (average, eight) were made from the edge of the eyecup to the equator, and the preparation was then washed with ice-cold PBS containing 0.3% Tween 20.[41] For visualization of vessels, the eyecup was stained overnight at room temperature with Alexa Fluor 488—conjugated *Griffonia* (*Bandeiraea*) *simplicifolia* isolectin B4 (Invitrogen) at a dilution of 1:100. The eyecup was flat-mounted on Superfrost/Plus microscope slides (Fisher) in SlowFade Antifade reagent (Invitrogen) with the sclera facing down and the choroid facing up. Fluorescence images of choroidal flat-mounts were captured with a Zeiss AxioCam MRm camera and Zeiss AxioObserver.Z1 microscope. The CNV area was measured with the use of Image J software.

Spectral domain optical coherence tomography (SD-OCT). SD-OCT was performed with a Bioptigen system at 5 and 7 days after laser photocoagulation. Mice were anesthetized with Avertin (Sigma) and positioned on a custom cassette that allowed three-dimensional free rotation for alignment of the eye for imaging. Hydration with normal saline was used to preserve corneal clarity. The B-scan were performed with 100 horizontal, raster, and consecutive B-scan lines, each one composed of 1000 A-scans. The area size was 1.4 by 1.4 mm. The software was able to generate an en face fundus image with the reflectance information obtained from the OCT sections (volume intensity projection), so that a point-to-point correlation between OCT and fundus position was possible and accurate. For evaluation of the cross-sectional size of each lesion in OCT images, the sections passing through the center of the CNV were chosen. The center of the lesion was defined as the midline passing through the area of rupture of the retinal pigment epithelium and Bruch's membrane. This point was identified consistently with the use of the en face fundus reconstruction tool provided with the Bioptigen SD-OCT system. This software tool allows generation of a fundus image with the use of the average reflectivity from each single OCT A-scan. The axial interval in OCT images used to generate this reconstruction is customizable. We narrowed and positioned it to the level of the retinal pigment epithelium—choroid complex, so that the area of the retinal pigment epithelium—Bruch's membrane rupture was readily identifiable in the fundus image as a hyporeflective spot.[25]

Fluorescein angiography. Fluorescein angiography was performed with a camera and imaging system (TRC 50 VT camera and IMAGEnet 1.53 system, Topcon) at 5 and 7 days after laser photocoagulation. Photographs were captured with a 20-diopter lens in contact with the fundus camera lens after intraperitoneal injection of 0.1 ml of 2% fluorescein sodium (Akorn). Two retina specialists (J. S. and D. G. V) who did not contribute to laser photocoagulation or angiography evaluated the fluorescein angiograms in a masked manner at a single sitting. Lesions were graded according to a previously established scheme as follows: 0 (not leaky), faint hyperfluorescence or mottled fluorescence without leakage; 1 (questionable leakage), hyperfluorescent lesion without progressive increase in size or intensity; 2A (leaky), hyperfluorescence increasing in intensity but not in size; 2B (clinically significant leakage), hyperfluorescence increasing in intensity and in size.[42]

CYP eicosanoid and fatty acid analysis. Tissue and serum samples were collected 7 days after inducing CNV from ω-6 and ω-3 LCPUFA fed mice and prepared for LC-MS/MS analysis of the CYP-eicosanoid profile as described previously.[28] Briefly, the samples were mixed with internal standard (10 ng each of 20-HETE-d6, 14,15-EET-d8, and 14,15-DHETE-d11; from Cayman Chemicals) and subjected to alkaline hydrolysis followed by solid-phase extraction of the metabolites using Agilent Bond Elute Certify II columns. The metabolites were analyzed with an Agilent 1200 HPLC system on a Phenomenex Kinetex-C18 column (2.6 µm, 2.1×150 mm) using a solvent system of aqueous formic acid (0.1%) and acetonitrile. Gradient elution was started with 5% acetonitrile, which was increased within 10 minutes to 90% and held there for 10 minutes. The flow rate was set at 0.3 mL/min. The HPLC was coupled with an Agilent 6460 triplequad mass spectrometer with electrospray ionization source. Analysis of CYP eicosanoids was performed with Multiple Reaction Monitoring in negative mode exactly as described previously.[28] Results were calculated using the Agilent Mass Hunter Software. The metabolite concentrations are given in ng/ml serum or in ng/mg of retinal protein as determined with the Lowry method.

Fatty acid analysis was performed using aliquots of the samples after alkaline hydrolysis. The samples were neutralized and diluted 1:10 with methanol containing internal standards (C15:0, C21:0 50 µg, C20:4-d8, C18:2-d4 5 µg, C20:5-d5 and C22:6-d5 1 µg) and measured using the same instrument configuration as described above. The solvent gradient started at 30% acetonitrile and was increased to 98% over 11 min with a flow rate of 0.4 mL/min. The mass spectrometer was operated in negative Single Ion Monitoring mode to detect the following fatty acids ions C 12:0 (m/z 199), C 14:0 (227), C 14:1 n-9 (225), C 15:0 (241), C 16:0 (255), C 16:1 n-9 (253), C 18:1 n-9 (281), C 18:2 n-6 (279), C 18:2 n-6 (279), C 18:2-d4 (283), C 18:3 n-3 (277), C 18:3 n-6 (277), C 20:3 n-6 (305), C 20:4 d8 (311), C 20:4 n-3 (303), C 20:4 n-6 (303), C 20:5 n-3 (301), C 20:5-d5 (306), C 22:5 n-3 (329), C 22:5 n-6 (329), C 22:6 n-3 (327) and C 22:6-d5 (332).

RNA isolation and cDNA preparation. Total RNA was extracted from the retina or choroid, and that from six to 10 eyes was pooled to reduce biological variability. The tissue was lysed with a mortar and pestle in a solution containing RNAlater (Ambion), the lysate was passed through a QiaShredder column (Qiagen), and total RNA was then extracted with the use of an RNeasy Mini Kit (Qiagen). Portions of the RNA (1 µg) were treated with RNase-Free DNase Set (Qiagen) to remove any contaminating genomic DNA and were then subjected to RT with the use of random hexamer primers and SuperScript III reverse transcriptase (Invitrogen). The resulting cDNA samples were stored at −80° C. until further analysis.

Real-time PCR analysis. Real-time PCR analysis was performed with the use of the StepOne Real-Time PCR System (Applied Biosystems) and with the following mouse TaqMan gene expression assays (Applied Biosystems): Icam-1 (Mm00516023_m1), Vcam-1 (Mm01320970_m1), IL-6 (Mm00446190_m1), Il-1β (Mm00434228_m1), IL-10 (Mm01288386_m1), Tnf-α(Mm00443258_m1), Ccl2 (Mm00441242_m1), Csf-1r (Mm01266652_m1), Vegf-a (Mm01281449_m1), E-selectin (Mm00441278_m1), P-selectin (Mm01295931_m1), Pparγ (Mm01184322_m1), Gpr120 (Mm00725193_m1), sEH (Mm00514706_m1), and β-actin (Mm00607939_s1). All data were normalized by the corresponding abundance of β-actin mRNA.

Laser-capture microdissection. Eyes were embedded in OCT compound and rapidly frozen immediately after enucleation. They were cyrosectioned at a thickness of 16 µm under RNase-free conditions, and the sections were collected on RNase-free polyethylene naphthalate glass slides (Leica), dehydrated with 50, 75, and 100% ethanol washes, and stained with isolectin B4 (1:50 dilution in 1 mM CaCl$_2$). Chorioretinal vessels in CNV lesions were microdissected with the use of a Leica LMD 7000 system and were collected directly into RNA-stabilizing buffer from an RNeasy Micro Kit (Qiagen).[16,19] RNA was then extracted from the microdissected tissue with the use of this kit and was subjected to real-time PCR analysis as described above.

Fluorescence microscopy of macrophage infiltration. Macrophages (or microglia) were visualized in the retina or choroid of heterozygous CX3CR1-GFP mice. Seven days after laser burns, mice were humanely killed, and the eyes were removed and fixed in 4% paraformaldehyde for 60 minutes. The cornea and lens were removed, and the entire retina was carefully separated from the eyecup. Radial cuts (average, eight) were made from the edge of the eyecup to the equator and then washed with cold buffer (0.3% Tween 20 in PBS), and stained with Alexa Fluor 647-conjugated isolectin B4 (Invitrogen) at a dilution of 1:100. Fluorescent images of retinal and choroidal flatmounts were visualized with a Leica SP2 confocal microscope equipped with a 40× objective. A stack of optical sections was collected at intervals of 0.50 µm. Data are from 15 and 13 lesions of mice fed ω-6 or ω-3 LCPUFAs, respectively.

Immunoblot analysis. The retina and choroid were isolated from mice and were separately pooled (n=6 to 10) to reduce biological variability. The tissue was homogenized with a lysis buffer (Roche Diagnostics) containing protease inhibitors (Roche Diagnostics), and the homogenate was centrifuged at 16,200×g for 10 mm at 4° C. The protein concentration of the resulting supernatant was determined with a DC (detergent-compatible) protein assay (Bio-Rad), and samples (20 µg of protein) were then fractionated by SDS-polyacrylamide gel electrophoresis on a 4 to 20% gradient gel (Invitrogen). The separated proteins were transferred to a polyvinylidene difluoride membrane (Millipore), which was then incubated with StartingBlock Blocking Buffer (Thermo Fisher Scientific) before exposure overnight at 4° C. to rabbit polyclonal antibodies to PPARγ (1:200 dilution, Santa Cruz Biotechnology), to sEH (1:100, Cayman Chemical), or to β-actin (1:2000, Cell Signaling). The membrane was then washed three times (5 mm each time) with Tris-buffered saline containing 0.5% Tween 20 before incubation for 20 min at room temperature with horseradish peroxidase—conjugated goat antibodies to rabbit immunoglobulin G (1:2,000, Cell Signaling). The membrane was again washed three times (5 min each time) with the same wash solution, after which immune complexes were visualized with the use of ECL reagents (GE Health Care) and then quantitated by densitometry with the use of ImageJ.

Measurement of PPARγ activity. The retinas (n=8) of mice were pooled to reduce biological variability and were homogenized in an ice-cold hypotonic buffer (ActiveMotif) for preparation of a nuclear fraction. The nuclear extract (20 µg of protein) was assayed for PPARγ activity with the use of an ELISA-based TransAM kit (ActiveMotif).

ELISAs for ICAM-1, E-selectin, and VEGF. The retina and choroid were isolated from mice and separately pooled (n=6 to 10) to reduce biological variability. Tissue homogenates were prepared and centrifuged as described above for immunoblot analysis. Equal amounts of supernatant protein were then assayed for ICAM-1, E-selectin, or VEGF with the use of ELISA systems (Novus Biologicals for ICAM-1; R&D Systems for E-selectin and VEGF). Each assay was performed a minimum of three times in triplicate.

Autoperfused microflow chamber assay. Leukocyte rolling velocity was analyzed using the autoperfused microflow chamber assay.[33,43] In brief, translucent microchambers (0.4×0.04×50 mm; VitroCom) were coated overnight at 4° C. with either recombinant murine P-selectin, or combination P-selectin and ICAM1 (R&D Systems) at a concentration of 5 µg/ml each. The microchambers were then connected at both ends to biocompatible polyester tubing (PE10, Becton Dickinson). Thereafter, both the tubing and microchamber were incubated with 0.1% bovine serum albumin (Sigma-Aldrich) for 1 h to block nonspecific leukocyte interaction with their inner surfaces. The free ends of the tubing were then connected microsurgically to the right carotid artery and left jugular vein of an anesthetized mouse. In this system, blood flows from the carotid artery into the biocompatible inlet tubing, passes through the microchamber, and reenters the animal's body via the outlet tubing and jugular vein. The rate of blood flow is regulated by adjustment of the diameter of the inlet tubing with a screw valve. Microtransducers (Harvard Apparatus) attached to the chamber by three-way connectors embedded before and after the microchamber allow the continuous measurement of blood pressure. The analog output of the microtransducers unit was digitalized with an A/D converter (ML785 PowerLab/8SP, ADInstruments) connected to a PC computer running CHART V7 software (ADInstruments). The measured values at the inlet and outlet of the microchamber were used to calculate the pressure drop ($\Delta P$). The shear stress ($\tau$) was derived from $\Delta P$ as previously descried.[33,43] Leukocyte rolling on immobilized adhesion molecules was observed with an upright, fixed-stage intravital microscope (Leica) and was videotaped with the use of a monochromic device camera (DFC 360 FX, Leica microsystems) for subsequent analysis. Ten different fields of view were recorded for at least 30 seconds. Leukocyte rolling velocity was determined from the displacement of individual cells interacting with the chamber surface over time ($\Delta d/\Delta t$). The displacement of leukocytes was determined using image J software 1.46 (NIH). Flux was defined as the number of interacting leukocytes per field of view, averaged over 10 independent field of views. To account for the hemodynamic conditions within the chamber, the blood pressure before the inlet and after the outlet of the chamber was measured, from which the drop of pressure $\Delta p$ and the shear stress were derived Isolation of PBLs for flow cytometric analysis. Blood freshly collected from the mouse heart with an EDTA-treated syringe was incubated for 30 min on ice with phycoerythrin-conjugated rat monoclonal antibodies to CD11b (M1/70, BD Biosciences) or to CD18 (C71/16, BD Biosciences), or with isotype control antibodies, at a ratio of 1 µg per $1\times10^6$ total cells. Red blood cells were lysed with the use of Easy-Lyse (Leinco Technologies), and the remaining cells were isolated by centrifugation and resuspended in PBS on ice for immediate flow cytometric analysis. PBLs were gated according to their characteristic forward and side scatter with the use of a Cytomics FC500 instrument (Beckman Coulter), and data were analyzed with FlowJo 10.0 software (Beckman Coulter).

Preparation of ocular-infiltrating cells and blood for flow cytometric analysis. To examine phenotypes, blood and ocular-infiltrating cells were prepared as described previously (Gautier et al., J Immunol. 2012; 189:2614-2624; Tsutsumi et al., J. Leukoc. Biol. 2003;74:25-32). Three days after CNV induction, mouse blood was collected by nonterminal submandibular or terminal cardiac puncture, and red blood cells were lysed with the use of Easy-Lyse (Leinco for immediate flow cytometric analysis. The eyes were enucleated, and the posterior segment of eye including sclera, choroid, and retina was disrupted with scissors and then shaken in medium supplemented with 0.5 mg/ml Collagenase type D (Boehringer Mannheim, Germany) at 37° C. for 40 min. As the basic medium, we used RPMI 1640 (Gibco Laboratories, Grand Island, NY) with 10% fetal bovine serum (Gibco Laboratories), 100 U/ml penicillin, 100 µg/ml streptomycin, $5\times10^{-5}$ M 2-mercaptoethanol, and 5 mg/ml HEPES buffer. The supernatants were collected, passed through a metal mesh, and washed three times, and viable cells were thus obtained. Surface staining was performed in the presence of Fc-blocking Abs (2.4G2). PE-Cy7 conjugated anti-CD115 mAb (AFS98) was purchased from eBioscience. APC conjugated anti-Ly-6G/Ly-6C mAb (RB6-8C5) was purchased from Biolegend. Data were acquired using a flow cytometer LSR II (BD Biosciences) and analyzed with FlowJo software (Tree Star, Ashland, Oreg.).

Statistical analysis. Data are presented as means±s.e.m. or s.d. and were analyzed with Student's t test for comparisons between two groups, indicated by * symbols) or Dunnett's test (for comparisons among more than two groups, indicated by † symbols). A P value of <0.05 was considered statistically significant.

Example 1

Cytochrome P450-Dependent Epoxymetabolites of ω-3 Long Chain Polyunsaturated Fatty Acids Promote Choroidal Neovessel Resolution To study the effect of ω-3 LCPUFAs on CNV, mice were fed one of two experimental diets: 1) a diet containing ω-3 LCPUFAs [1% DHA and 1% EPA, with no arachidonic acid (AA)], or 2) a diet devoid of ω-3's but containing ω-6 LCPUFAs (2% AA), as previously described.[17] These diets were given 2 weeks prior to laser CNV induction. Given that the typical intake of ω-3 LCPUFAs in the United States (100 to 200 mg/day) provides ~0.05 to 0.1% of total calories, the amount of these fatty acids in the experimental diet is physiological and attainable by patients. To evaluate the effect of LCPUFAs on CNV formation, choroidal flat-mount preparations were first examined after lectin staining for blood vessels after CNV induction.[23,24] Lesion size at 5 days after photocoagulation (previously shown to be the time of peak size and severity[25]) did not differ significantly between mice fed ω-3 or ω-6 LCPUFAs, whereas size at 7 days was significantly smaller in animals fed ω-3 LCPUFAs (FIG. 1a,b), indicating that ω-3 LCPUFAs promote disease resolution in the laser-induced AMD model.

Figure 1C:
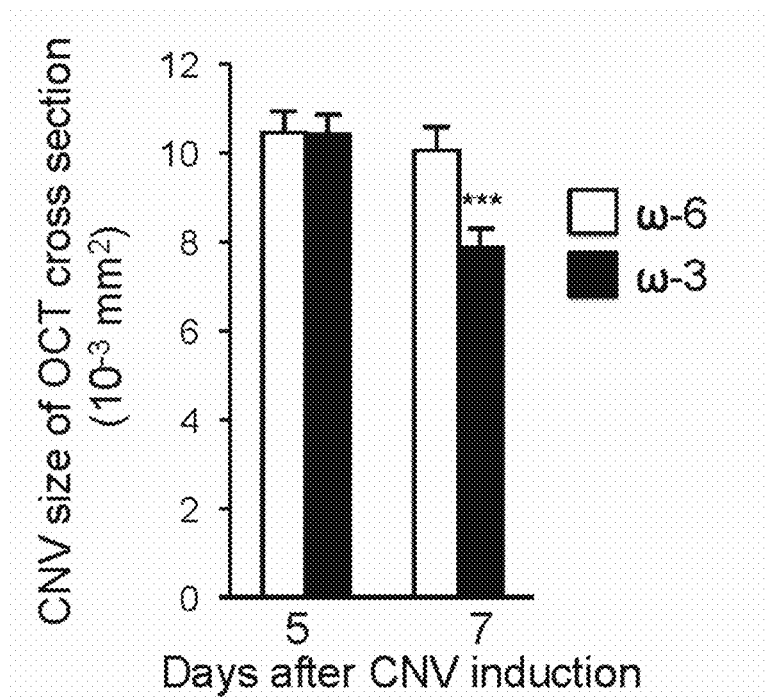
Figure 1D:
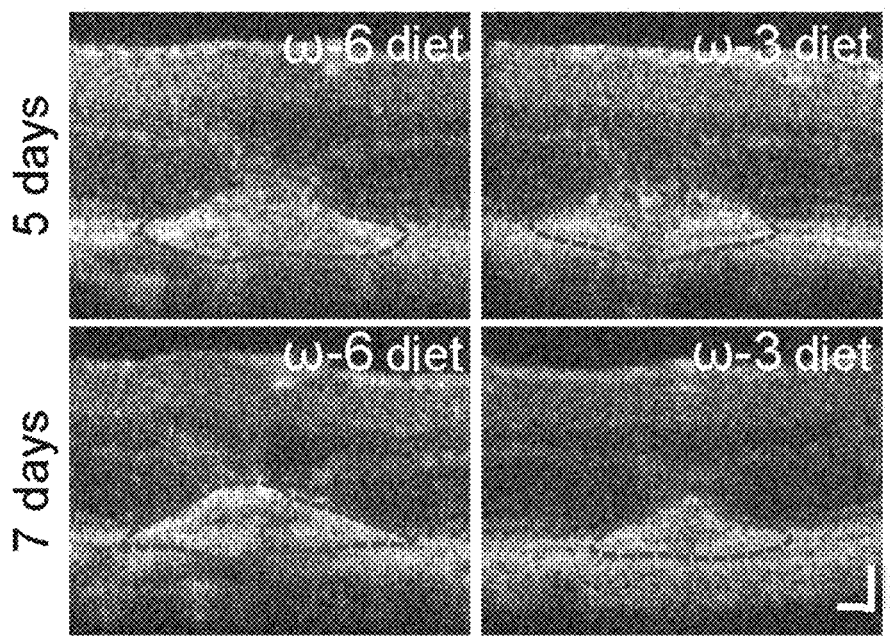

Spectral domain optical coherence tomography (SD-OCT) allows detailed and noninvasive evaluation of the retinal architecture in vivo, and has been found to reflect retinal morphological changes during AMD.[22,26] Thus, SD-OCT was used to determine the cross-sectional area of CNV lesions in mice fed either ω-3 or ω-6 LCPUFAs. Five days after CNV induction, lesion size did not differ between mice fed either experimental diet. However, 7 days post CNV induction, the lesion area was significantly smaller in mice fed ω-3 LCPUFAs compared to mice fed ω-6 LCPUFAs (FIG. 1c,d), further supporting the role of ω-3 LCPUFAs in CNV lesion resolution.

Figure 1E:
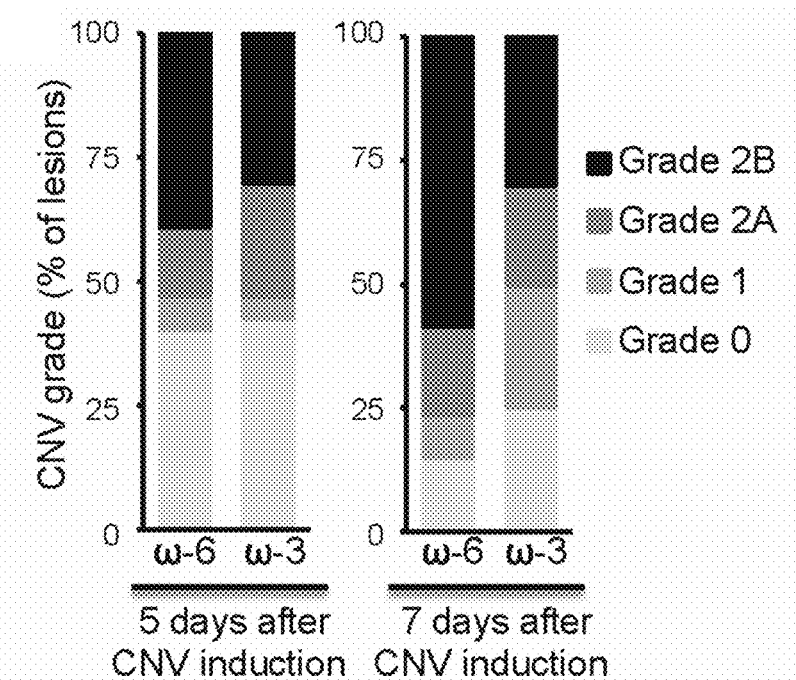
Figure 1F:
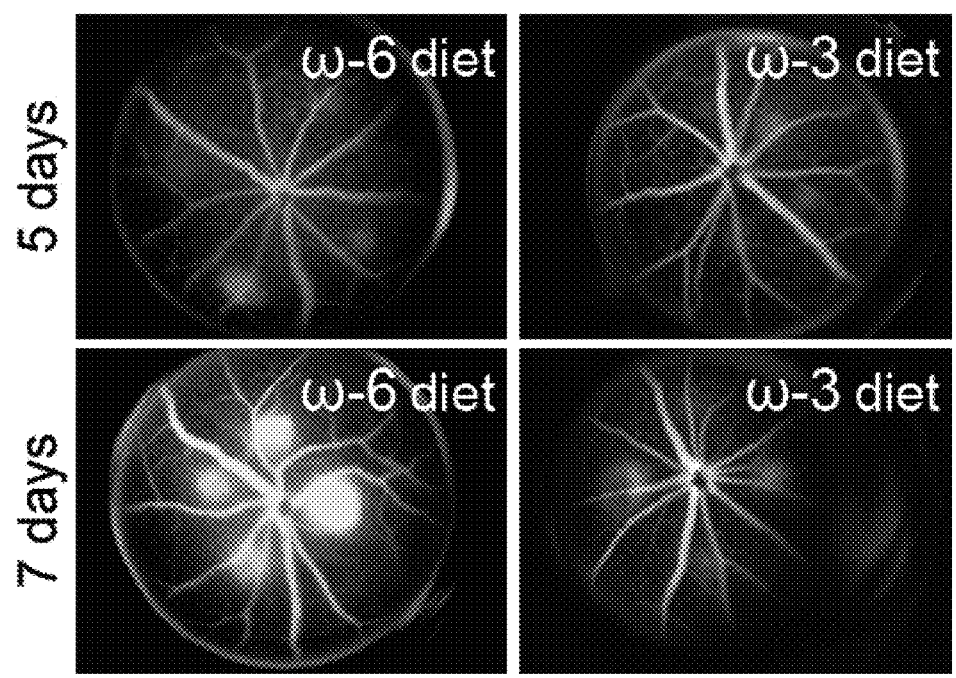

Vascular leakage in neovascular AMD eyes may lead to retinal pigment epithelium detachment along with subretinal or intraretinal edema related to visual disturbances and loss of vision. The effect of dietary intake of ω-3 LCPUFAs on the vascular leakage from CNV lesions was assessed. Fluorescein angiography revealed that the extent of leakage from the new (pathologic) choroidal vessels at both 5 and 7 days after CNV induction was less pronounced in ω-3-fed mice LCPUFAs than in ω-6-fed mice (FIG. 1e,f). The incidence of clinically significant (grade 2B) CNV lesions at 7 days after photocoagulation was thus only 30.0% in mice receiving ω-3 LCPUFAs vs. 58.3% for mice fed ω-6 LCPUFAs.

To gain mechanistic insight into the effect of dietary ω-3 LCPUFAs on CNV size, lipid profiles were analyzed by liquid chromatography—mass spectrometry/mass spectrometry (LC-MS/MS) of both the retina and serum in mice on either diet 7 days after CNV induction. The concentrations of the principal ω-3 LCPUFAs (EPA and DHA) and of total ω-3 LCPUFAs as well as the DHA/ω-6 docosapentaenoic acid (DPA) ratio were significantly increased, whereas the ω-6/ω-3 LCPUFA ratio was significantly decreased, in serum of ω-3-fed mice compared with the ω-6-fed mice counterparts (Table 1). EPA levels and DHA/ω-6 DPA ratios were also significantly increased, whereas the amounts of AA and ω-6 DPA were reduced, in the retinas of mice fed the ω-3 LCPUFA diet.

TABLE 1

Fatty acid composition (% of total fatty acids by weight) of serum and the retina at 7 days after CNV induction in mice fed a diet enriched in ω-6 or ω-3 LCPUFAs

|  | Serum | | | | | Retina | | | | |
| --- | --- | --- | --- | --- | --- | --- | --- | --- | --- | --- |
|  | ω-6 LCPUFA diet | | ω-3 LCPUFA diet | | P | ω-6 LCPUFA diet | | ω-3 LCPUFA diet | | P |
| Saturated FAs | | | | | | | | | | |
| PA C16:0 | 11.10 | (4.47) | 14.00 | (1.31) | 0.43 | 12.06 | (0.66) | 12.61 | (1.77) | 0.67 |
| SA C18:0 | 7.18 | (4.31) | 9.13 | (1.03) | 0.49 | 9.23 | (1.42) | 7.18 | (4.78) | 0.37 |
| Total ω-6 LCPUFAs | 18.28 | (8.63) | 23.13 | (2.28) | 0.45 | 21.87 | (1.93) | 20.59 | (3.58) | 0.43 |
| LA C18:2 n-6 | 16.82 | (6.67) | 17.89 | (1.25) | 0.76 | 2.49 | (0.21) | 4.70 | (2.42) | 0.16 |
| AA C20:4 n-6 | 27.58 | (9.01) | 9.90 | (1.03) | 0.07 | 12.18 | (0.67) | 9.40 | (0.84) | 0.0033 |
| DPA C22:5 n-6 | 0.50 | (0.17) | 0.06 | (0.01) | 0.044 | 0.23 | (0.01) | 0.04 | (0.01) | 0.0006 |
| Total ω-3 LCPUFAs | 44.90 | (15.37) | 27.85 | (2.10) | 0.16 | 14.90 | (0.77) | 14.14 | (2.72) | 0.53 |
| ALA C18:3 n-3 | 0.80 | (0.13) | 0.69 | (0.05) | 0.15 | 0.11 | (0.06) | 0.08 | (0.06) | 0.47 |
| EPA C20:5 n-3 | 0.13 | (0.07) | 2.85 | (0.11) | 0.0006 | 0.25 | (0.04) | 1.29 | (0.11) | 0.0006 |
| DHA C22:6 n-3 | 5.71 | (0.88) | 13.56 | (0.65) | 0.013 | 53.47 | (1.71) | 52.32 | (3.43) | 0.62 |
| Total | 9.31 | (3.62) | 16.52 | (0.74) | 0.044 | 53.82 | (1.74) | 53.68 | (3.46) | 0.98 |
| DHA/ω-6 DPA ratio | 19.81 | (0.38) | 235.84 | (36.73) | 0.0087 | 230.18 | (17.20) | 1335.91 | (365.04) | 0.01 |
| ω-6/ω-3 ratio | 5.46 | (0.05) | 1.63 | (0.06) | 0.0002 | 0.27 | (0.02) | 0.23 | (0.02) | 0.73 |

Data are means (s.d.) for 3 mice. Abbreviations not defined in text: PA, palmitic acid; SA, stearic acid; LA, linoleic acid; ALA, α-linolenic acid. P values were determined by Student's t test, and those of <0.05 are shown in bold.

Example 2

Figure 2B:
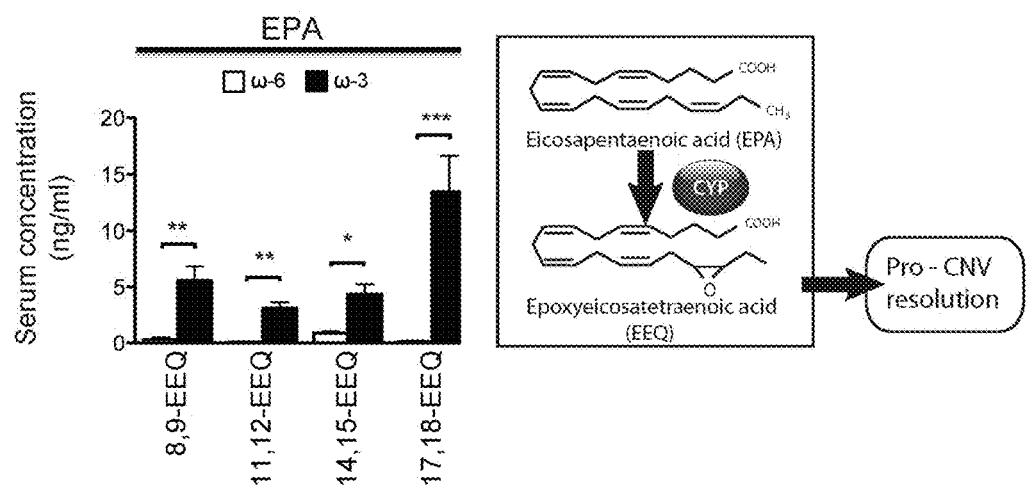
Figure 2C:
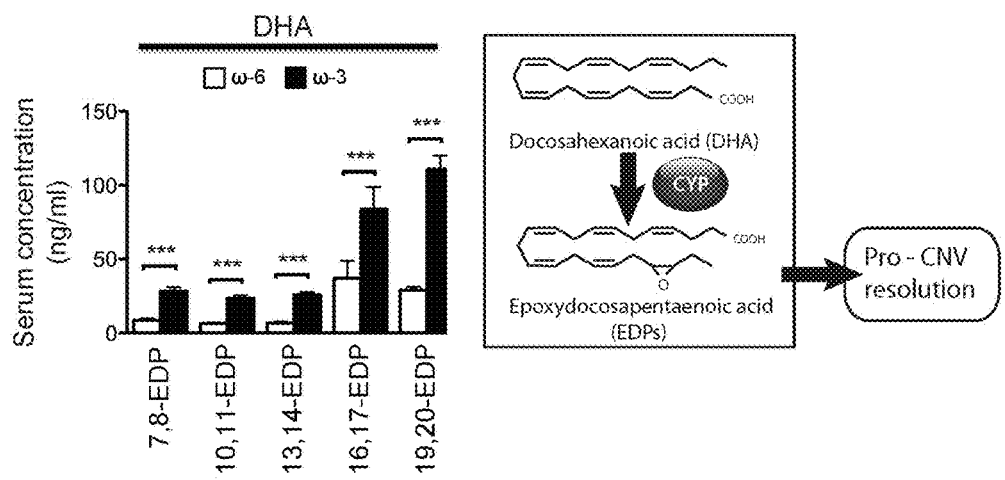
Figure 2D:
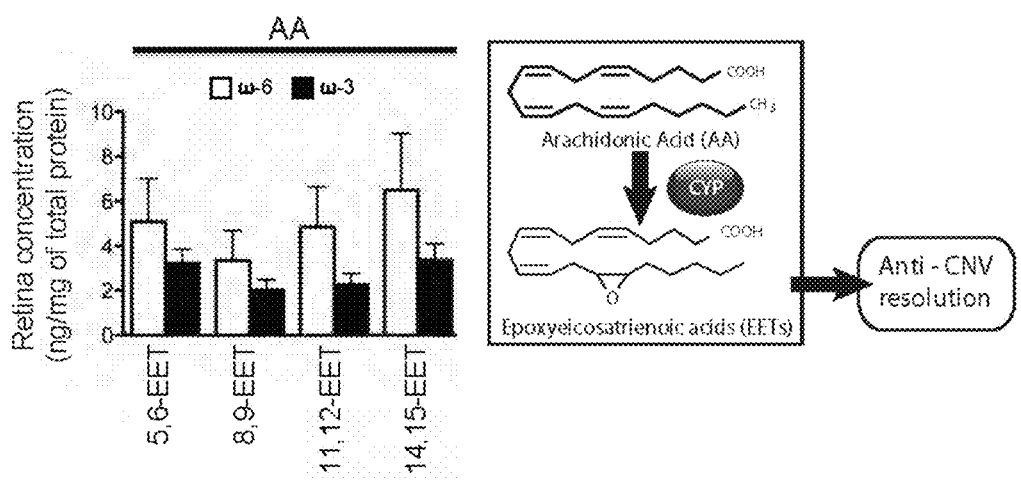
FIGS. 2D-F. Effects of dietary intake of ω-3 LCPUFAs on the profile of monoepoxides in the retina. (D-F) Fatty acid profiles derived from AA (D), EPA (E), and DHA (F) were determined for the retina (n=7) at 7-days after CNV induction in mice fed a diet enriched in ω-6 or ω-3 LCPUFAs. *$P<0.05$, **$P<0.01$. All quantitative data are means±SEM.
Figure 2E:
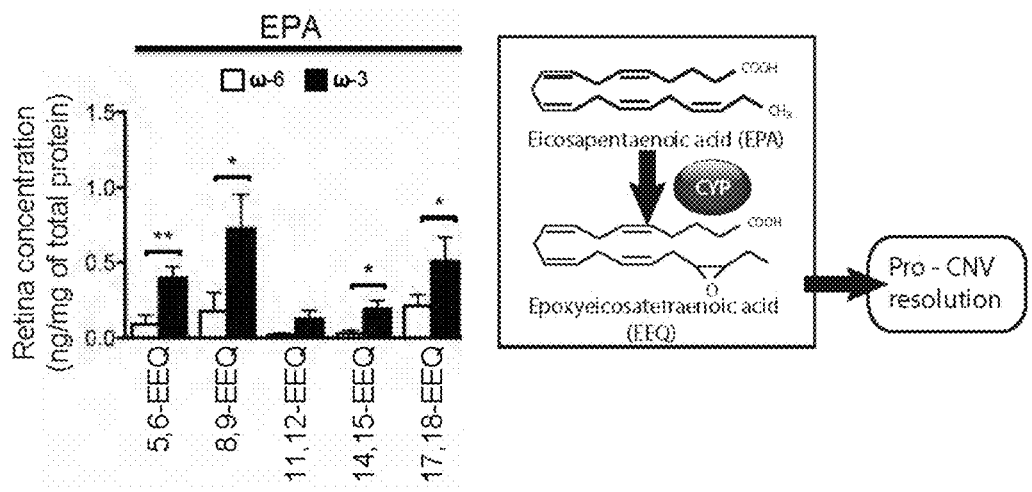
Figure 2F:
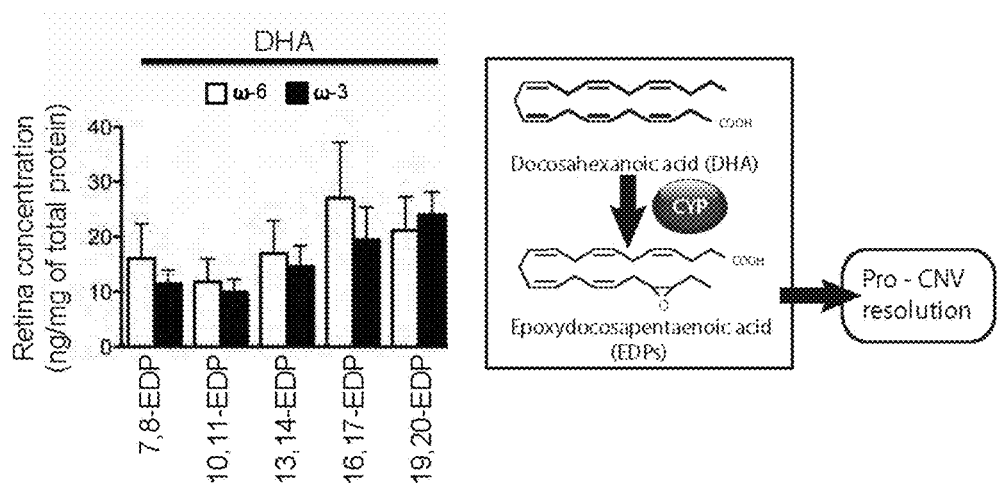

Identification of Significantly Regulated CYP Metabolites by LC-MS/MS in Mice Fed a Diet of Either ω-3 or ω-6 LCPUFAs EPA and DHA are efficient alternative substrates of the AA metabolizing CYP isoforms and are predominantly epoxidized at their ω-3 double bond to yield 17,18-epoxyeicosatetraenoic acid (17,18-EEQ) and 19,20-epoxydocosapentaenoic acid (19,20-EDP) as main products,[27-29] which have the potential to ameliorate CNV. LC-MS/MS was used to measure the amounts of endogenous CYP-epoxyeicosanoids in the serum and retina at 7 days after CNV induction in mice fed ω-3 or ω-6 LCPUFAs. The serum levels of AA-derived 14,15-dihydroxyeicosatrienoic acids (DHET)+epoxyeicosatrienoic acid (EETs; 5,6- 8, 9-, 11,12- and 14,15-) examined were significantly reduced (FIG. 2A), whereas those of EPA-derived EEQs (8,9-, 11,12-, 14,15- and 17,18-EEQ) and DHA-derived EDPs (7,8-, 10,11-, 13,14-, 16,17- and 19,20-EDP) were significantly increased in ω-3 LCPUFA fed mice (FIGS. 2B, C). Unlike the serum, the retinal levels of AA and DHA derived epoxyeicosanoids were unchanged (FIGS. 2D and F). Only the EPA-derived EEQs-were significantly increased in ω-3-fed mice (FIG. 2E). These results indicate that in mice on a short-term dietary regimen, the serum level of systemic CYP metabolites has an increased contribution to disease resolution compared to those found within the retina.

Example 3

Cytochrome P450 Lipid Metabolites Derived from ω-3 LCPUFAs Decrease CNV Lesion Size To assess the effect of CYP lipid metabolites derived from ω-3 LCPUFAs on choroidal neovascularization, 17,18-EEQ and 19,20-EDP were evaluated in the laser-induced AMD model. Exogenous 17,18-EEQ or 19,20-EDP was administered at levels comparable to their serum concentration identified by LC-MS/MS in mice on a ω-3 diet (FIG. 3A and E). Intraperitoneal injection of 17,18-EEQ conferred significant and dose-dependent protection from laser-induced CNV, as assessed in choroidal flatmount and SD-OCT (FIG. 3B and C). Additionally, 17,18-EEQ significantly decreased vascular leakage after CNV induction (FIG. 3D). Comparable effects were observed in the DHA derived 19,20-EDP metabolite. Here, intraperitoneal administration of 19,20-EDP conferred significant protection against both CNV formation and against vascular leakage (FIG. 3, F-H). This data suggest that ω-3 LCPUFA-derived CYP pathway eicosanoids have crucial roles as key lipid mediators that limit laser-induced CNV and promote disease resolution.

Example 4

PPARγ Expression and Activation are Elevated in ω-3 LCPUFA Fed Mice

Figure 4A:
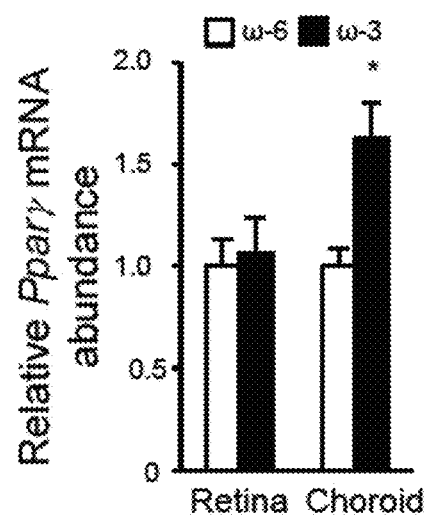
Figure 4B:
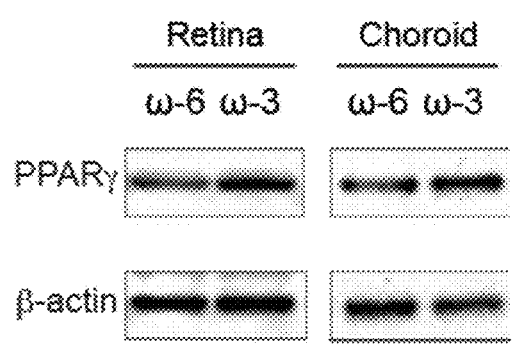
Figure 4E:
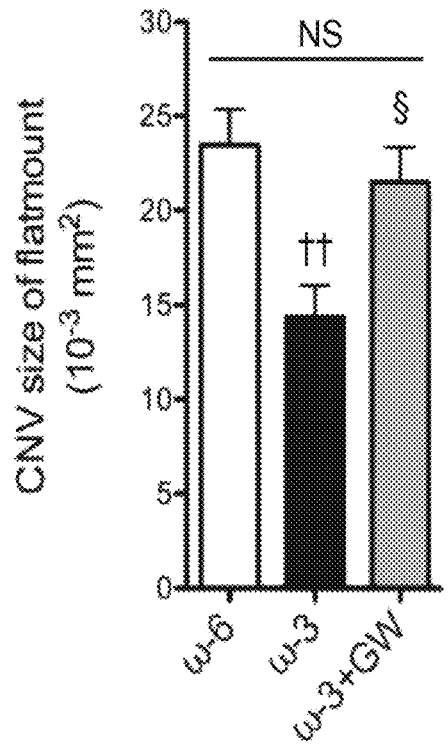
Figure 4F:
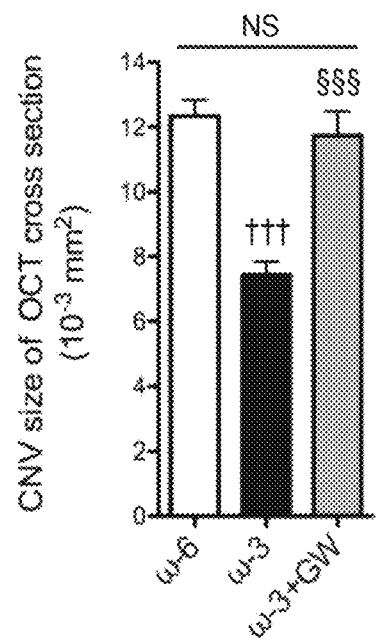
Figure 4G:
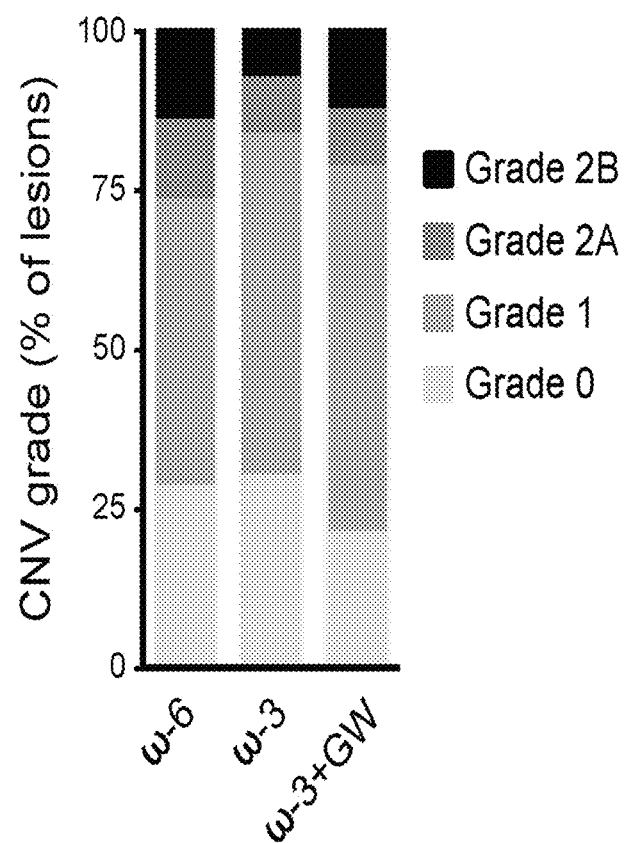
Figure 4H:
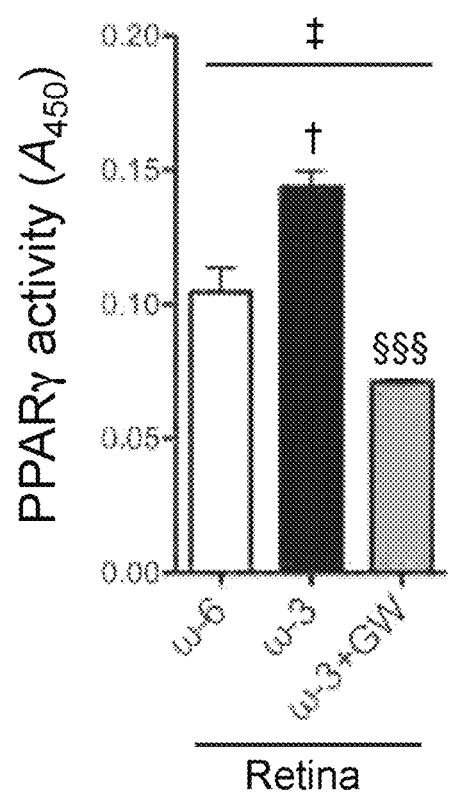
Figures 4I, 4J:
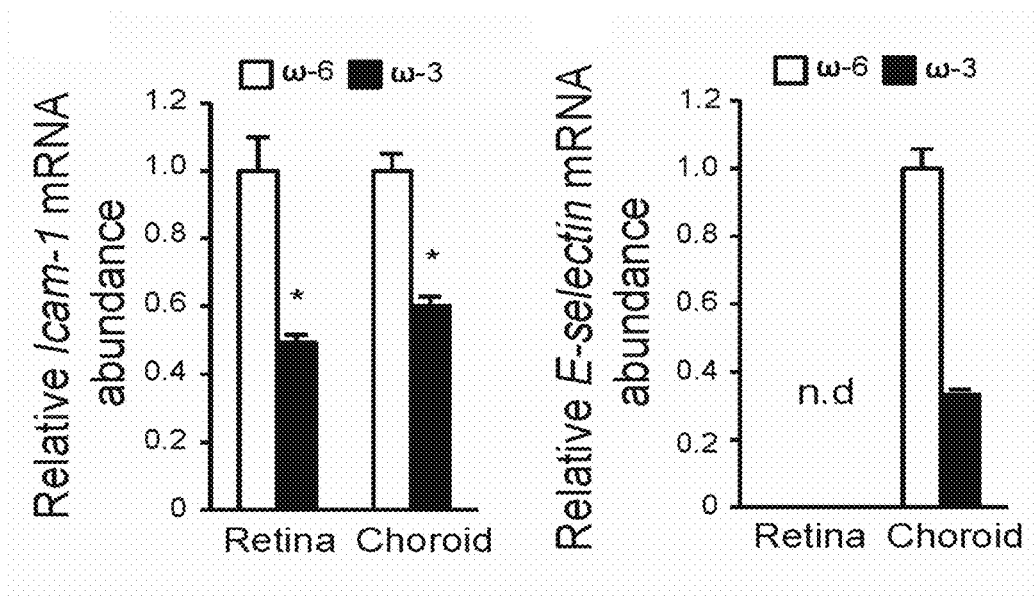
FIGS. 4I-N. Down-regulation of adhesion molecules are associated with suppression of laser-induced CNV by dietary ω-3 LCPUFAs. (I and J) Real-time PCR analysis of Icam-1 (I) and E-selectin (J) mRNAs in the retina and choroid at 7-days after the induction of CNV in mice fed ω-6 or ω-3 LCPUFAs (n=3). n.d, not detected. (K and L) Real-time PCR analysis of Vcam-1 (K), and P-selectin (L) mRNAs in the retina and choroid at 7-days after the induction of CNV in mice fed ω-6 or ω-3 LCPUFAs (n=3). All data are means±SEM. (M and N) ELISA-based determination of the amounts of ICAM-1 (M) and E-selectin (N) in the choroid at the indicated times after CNV induction in mice fed ω-6 or ω-3 LCPUFAs (n=4). All data are means±SEM *P<0.05, P<0.01, *P<0.001.

To further decipher the mode of action that dietary intake of ω-3 LCPUFAs have in disease resolution, the peroxisome proliferator—activated receptor-γ (PPARγ) pathway (Bensinger and Tontonoz, Nature. 2008;454:470-477) was investigated. Previous studies demonstrated that ω-3 LCPUFAs attenuate retinal neovascularization via a mechanism involving the activation of PPARγ, an endogenous ω-3 LCPUFA receptor (Stahl et al., Circ Res. 2010;107:495-500). The contribution of each diet on PPARγ expression was examined in mice with laser-induced CNV. At 7-days after CNV induction real-time PCR showed that the amount of Pparγ in the choroid was significantly increased in ω-3-fed mice compared with their ω-6-fed counterparts (FIG. 4A), whereas immunoblot analysis revealed that the abundance of PPARγ protein was significantly increased in both the retina and choroid in ω-3-fed mice (FIGS. 4B and C). The transactivation activity of PPARγ in retinal nuclear extracts was also significantly higher in ω-3-fed mice (FIG. 4D). These findings suggest that dietary intake of ω-3 LCPUFAs facilitates PPARγ signaling and is involved in the resolution of laser induced CNV. To assess the effect of PPARγ signaling in ω-3-fed mice on CNV regression, CNV lesions were examined with or without a potent PPARγ inhibitor. Pharmacological inhibition of PPARγ with the specific inhibitor GW9662 (Ambati and Fowler, Neuron. 2012;75: 26-39) significantly reduces the protective effects of ω3-LCPUFAs on CNV size (FIGS. 4E and F) and leakage (FIG. 4G). Notably, pharmacological inhibition of PPARγ also significantly reduces the activity of PPARγ in the retina of ω-3-fed mice (FIG. 4II). These results suggest that PPARγ is a major pathway through which ω-3 LCPUFAs exert their beneficial effects on CNV regression.

Example 5

Figures 4K, 4L:
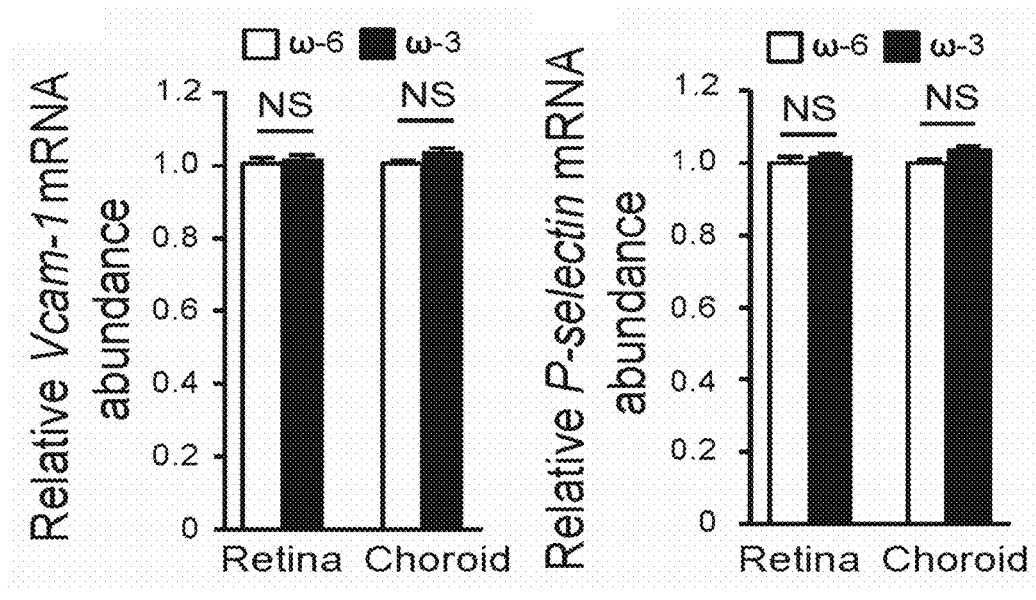
Figure 4M:
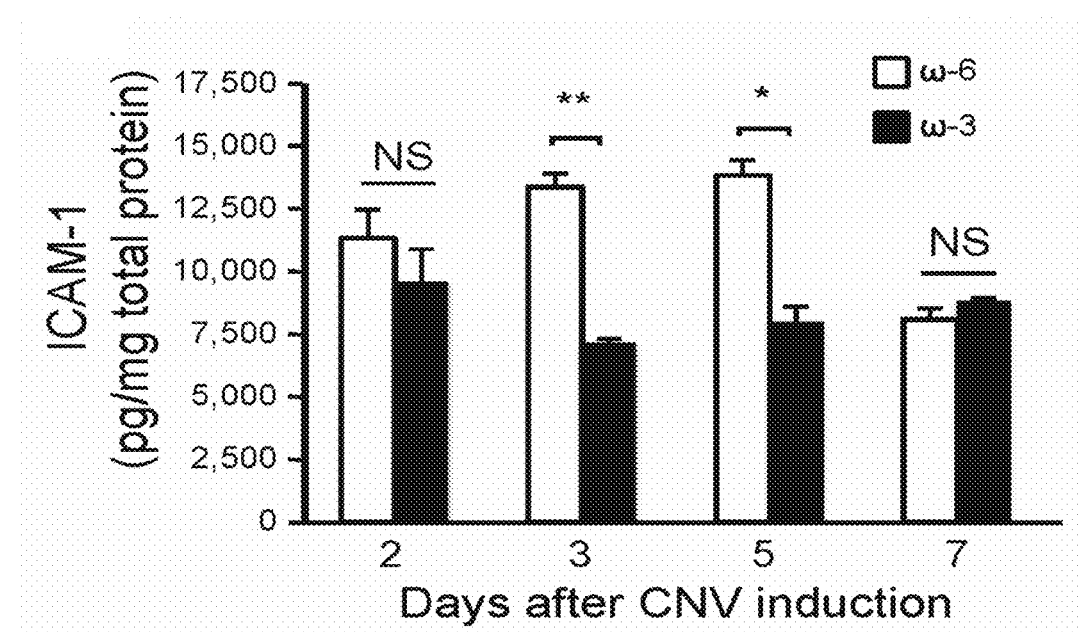
Figure 4N:
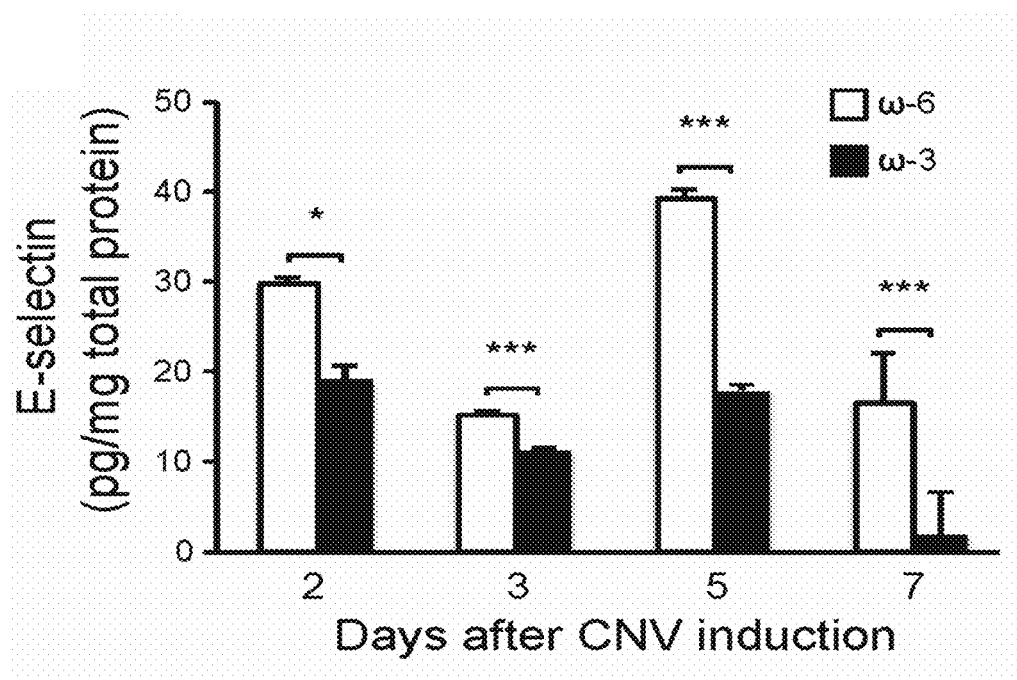
Figure 5A:
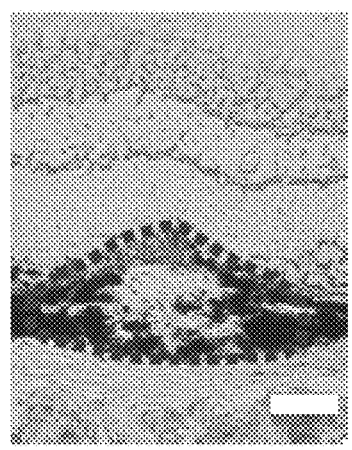

Dietary Intake of ω-3 LCPUFAs Suppresses ICAM-1 and E-Selectin Expression in CNV Lesions It has been previously demonstrated that ω-3-fed mice downregulate, in a PPARγ-dependent fashion, key adhesion molecules in retinal neovessel (Stahl et al., Circ Res. 2010; 107:495-500; Im et al., Prog Lipid Res. 2012;51:232-237). The effects of dietary ω-3-LCPUFAs on adhesion molecule expression were examined in the laser-induced CNV model. Seven days after the induction of CNV, mice fed ω-3 LCPUFAs had significantly reduced levels of Icam-1 and E-selectin in both the retina and choroid compared to mice on an ω-6 LCPUFA diet (FIGS. 4I and J). In contrast, there was no difference in the amounts of Vcam-1 or P-selectin in the retina or choroid in either of the two treatment groups (FIGS. 4K and L). Between 2- and 7-days after CNV induction, the protein levels of these adhesion molecules in the choroid were also significantly reduced in ω-3-fed mice (FIGS. 4M and N). Laser-capture microdissection of the CNV lesions confirmed the diminished levels of Icam-1 and E-selectin in ω-3-fed mice was localized to these lesions (FIGS. 5A-C). These data imply that dietary ω-3 LCPUFAs regulate adhesion molecule expression and subsequent recruitment of systemic leukocytes to the CNV lesion.

Example 6

Functional Downregulation of Both ICAM-1 on Endothelial Cells and ICAM-1 Ligand on the Surface of Leukocytes is Mediated by Intake of ω-3 LCPUFAs Systemic leukocyte recruitment to the CNV lesion has been postulated to worsen the disease (Ishida et al., Nat Med. 2003;9:781-788). To assess the impact of ω-3 LCPUFAs on systemic leukocyte recruitment to the CNV site, the rolling velocity of peripheral blood leukocytes (PBLs) was measured at 3-days after CNV induction (the height of immune cell infiltration in this model (Noda et al., Faseb J.

Figure 5F:
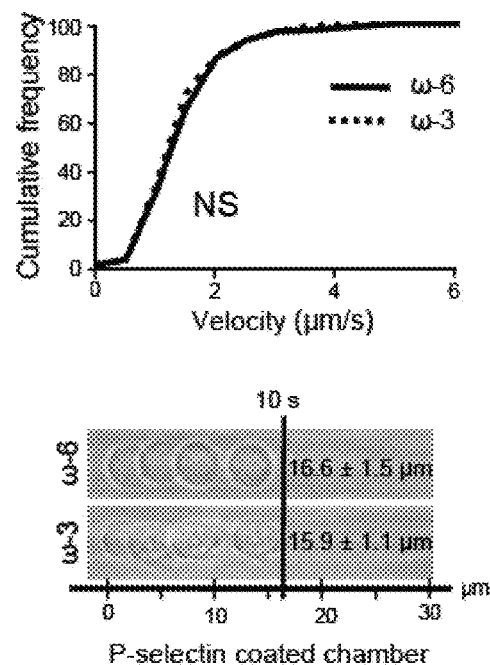

2008;22:2928-2935)) with the use of the autoperfused microflow chamber coated with, P-selectin, or the combination of P-selectin and ICAM-1. The rolling velocity of PBLs on the P-selectin and ICAM-1 coated chambers were significantly greater for mice fed ω-3 LCPUFAs (1.87±0.18 μm/s) than for those fed the ω-6 LCPUFA diet (1.24±0.07 μm/s) (FIG. 5D) in a PPARγ-dependent fashion (FIG. 5E). PBLs from both groups of dietary fed mice rolled at similar velocities on immobilized P-selectin (FIG. 5F).

To account for the hemodynamic conditions within the chamber, the blood pressure before the inlet and after the outlet of the chamber was measured, from which the drop of pressure, Δp, and the shear stress were derived. The average shear values were stable among all experimental groups (Table 2). No difference was noted in the number of interacting leukocytes per field of view between the two groups on either P-selectin, E-selectin or combined P-selectin and ICAM-1 coated chambers (FIGS. 5I and J). These data were thus suggestive of functional down-regulation of both ICAM-1 on endothelial cells and the ICAM-1 ligand on the surface of leukocytes in mice fed the ω-3 LCPUFA diet.

Figure 5G:
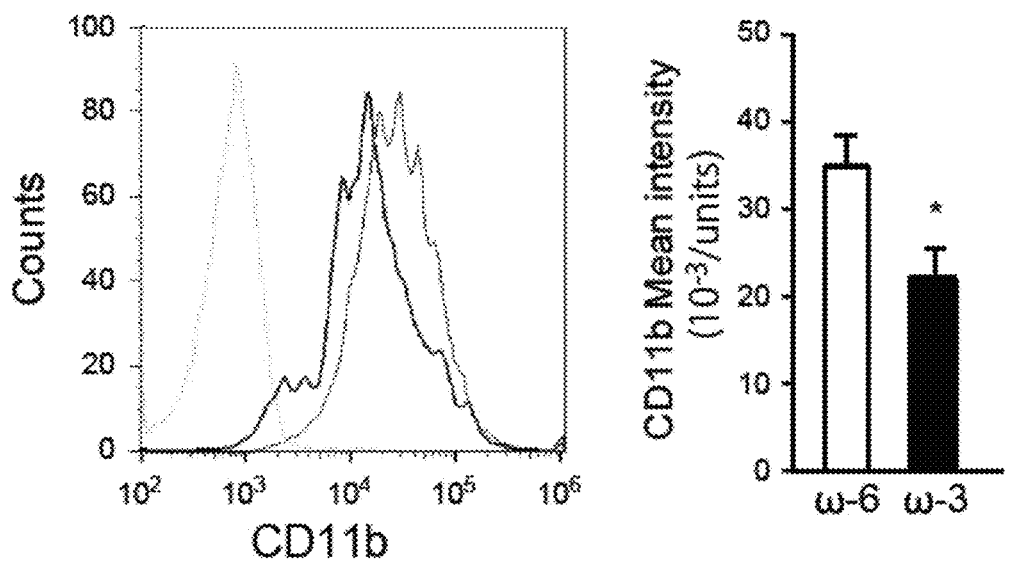

To further investigate the increase in ICAM-1 dependent rolling velocity of PBLs from mice fed ω-3 LCPUFAs, the expression of the ICAM ligands, CD11b and CD18, was measured on circulating leukocytes. Flow cytometry revealed that the surface expression levels of both CD11b and CD18 on PBLs were significantly lower for mice fed ω-3 LCPUFAs than for those fed the ω-6 LCPUFA diet (FIGS. 5G and H), consistent with the notion that the increased rolling velocity of leukocytes from the former mice is attributable, at least in part, to down-regulation of CD11b and CD18.

Figure 6A:
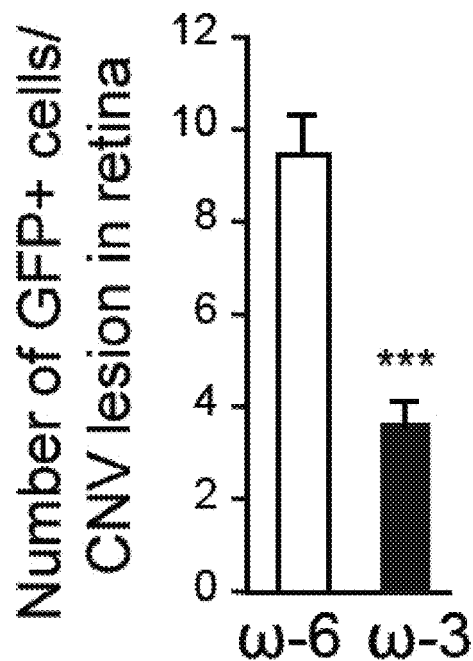
FIGS. 6A-B. Dietary ω-3 LCPUFA intervention suppresses macrophage invasion in CNV lesions. (A) Quantitation of macrophage (GFP+cell) invasion in CNV lesions at the back surface of the retina in retinal flatmount preparations at 7-days after CNV induction in mice fed a diet enriched in ω-6 or ω-3 LCPUFAs. The preparations were from Cx3cr1$^{GFP/+}$ mice, which express enhanced GFP specifically in monocytes, dendritic cells, and microglia, and were stained with isolectin B4 to detect endothelial cells (magenta fluorescence). Data are means±SEM for 15 and 13 lesions of mice fed ω-6 or ω-3 LCPUFAs, respectively. *P<0.001. (B) Quantitation of Macrophage invasion in CNV lesions in flatmount preparations of the choroid examined as in (A). Data are means±SEM for 15 and 13 lesions of mice fed ω-6 or ω-3 LCPUFAs, respectively. P<0.01.
Figure 6B:
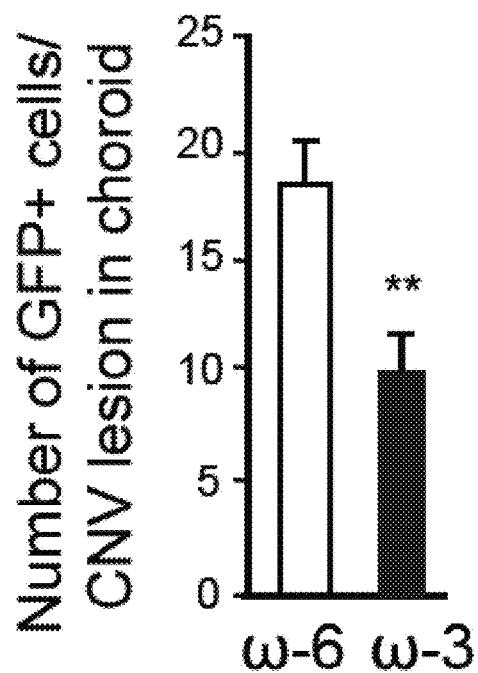
Figure 6C:
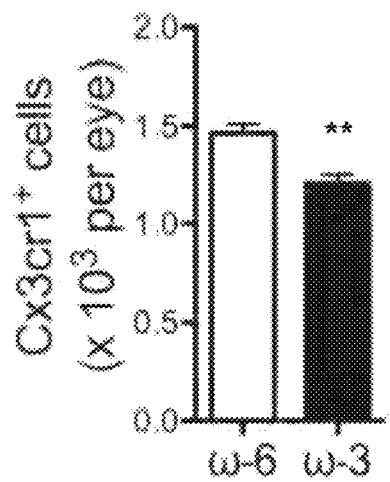
FIGS. 6C-H. Phenotype analysis of leukocytes for mice fed ω-6 or ω-3 LCPUFAs. (C) Cx3cr1 positive cell counts in the retina/choroid at 3-days after CNV induction in mice fed ω-6 (n=8) or ω-3 (n=8) LCPUFAs. (D) FACS plot illustrating the gating strategy used for inflammatory macrophages (Mφ; CD115+Ly-6C−) and Ly-6Chi monocytes (CD115+Ly-6C+) in the retina/choroid at 3-days after CNV induction in mice fed ω-6 (n=8) or ω-3 (n=8) LCPUFAs. (E) Ly-6Clow macrophage and Ly-6Chigh monocyte counts in the retina/choroid at 3-days after CNV induction in mice fed ω-6 (n=8) or ω-3 (n=8) LCPUFAs. (F) Cx3cr1 positive cell counts in blood at 3-days after CNV induction in mice fed ω-6 (n=4) or ω-3 (n=4) LCPUFAs. (G) FACS plot illustrating the gating strategy used for inflammatory macrophages (Mφ; CD115+Ly-6C−) and Ly-6Chi monocytes (CD115+Ly−6C+) in blood at 3-days after CNV induction in mice fed ω-6 (n=4) or ω-3 (n=4) LCPUFAs. (H) Ly-6Clow macrophage and Ly-6Chigh monocyte counts in blood at 3-days after CNV induction in mice fed ω-6 (n=4,) or ω-3 (n=4) LCPUFAs.
Figure 6D:
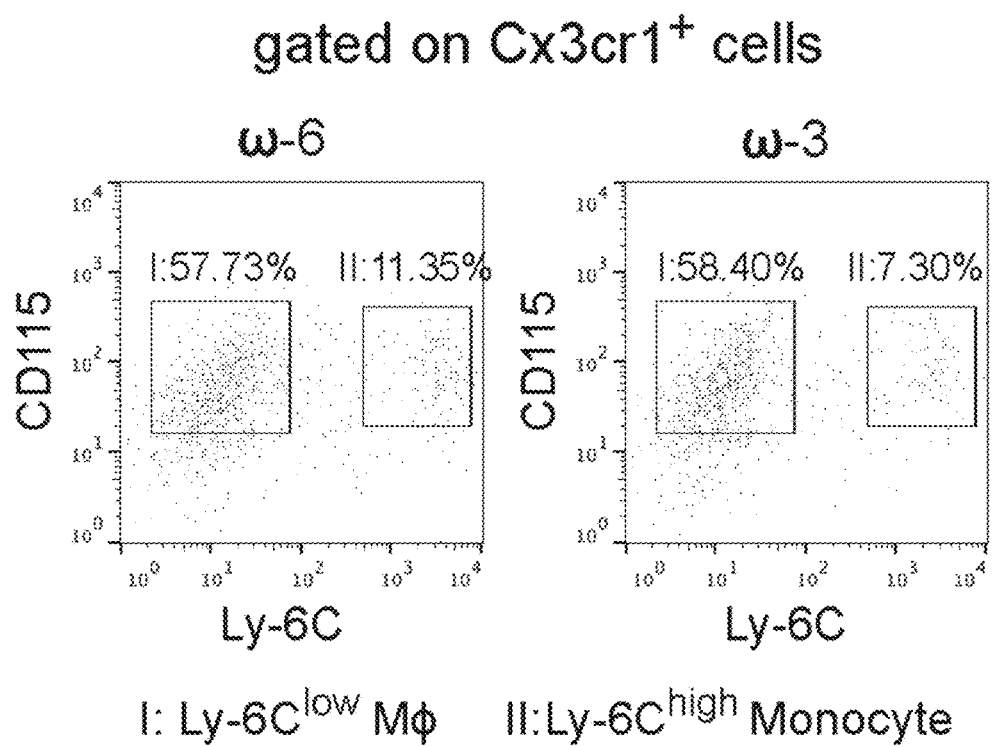
Figure 6E:
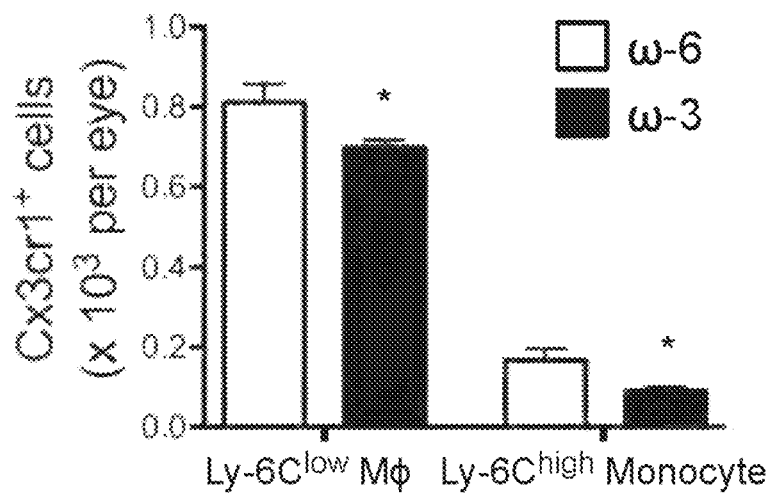
Figure 6F:
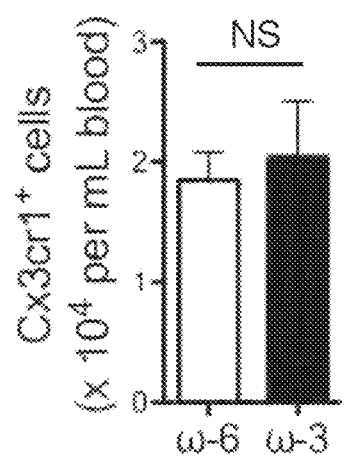
Figure 6G:
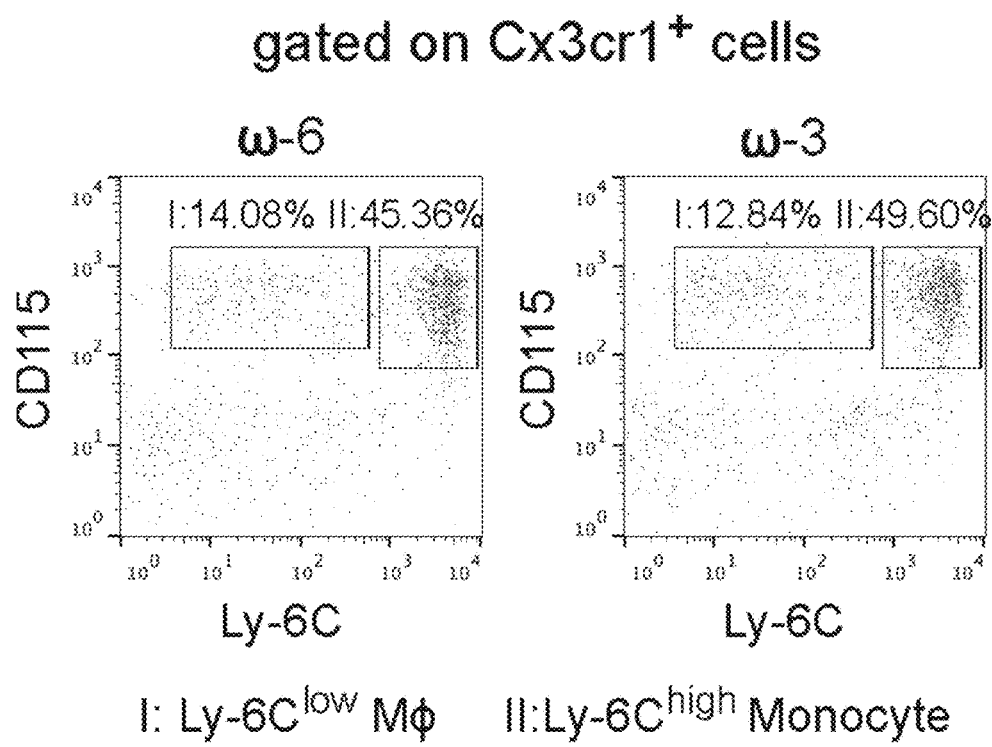
Figure 6H:
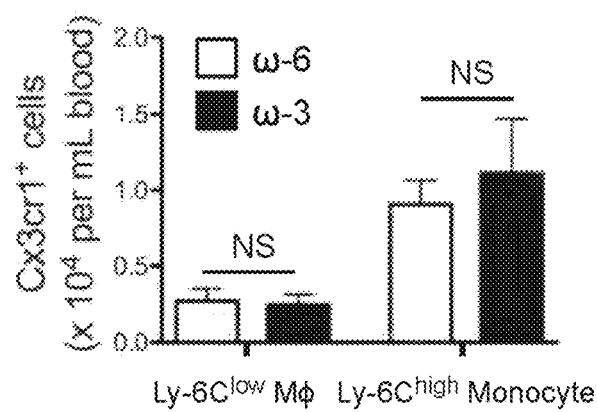

$Cx3cr1^{GFP/+}$ mice. These data suggest that ω-3 LCPUFAs are important in suppressing the recruiting of immune cells to the CNV lesion in the retina and choroid. To begin to identify the phenotype of Cx3cr1 positive cells in CNV disease the expression of Ly-6C was investigated by FACS analysis in the retina/choroid as well as in the circulation of ω-3-fed mice. Accumulation of retinal/choroidal Cx3cr1 positive cells, $Ly-6C^{low}$ macrophages and $Ly-6C^{high}$ monocyte were significantly reduced in mice fed with ω-3 LCPUFAs diet compared to those on ω-6-feed (FIGS. 6C-E). In contrast, blood Cx3cr1 positive, $Ly-6C^{low}$ macrophage and $Ly-6C^{high}$ monocyte did not differ in mice with ω-3-fed mice nor ω-6-fed mice (FIGS. 6F-H). These results indicate that dietary intake of ω-3 LCPUFAs suppresses macrophage invasion into the CNV lesions.

Example 8

Dietary ω-3 LCPUFAs Suppress VEGF Expression in the Retina and Choroid

Figure 7A:
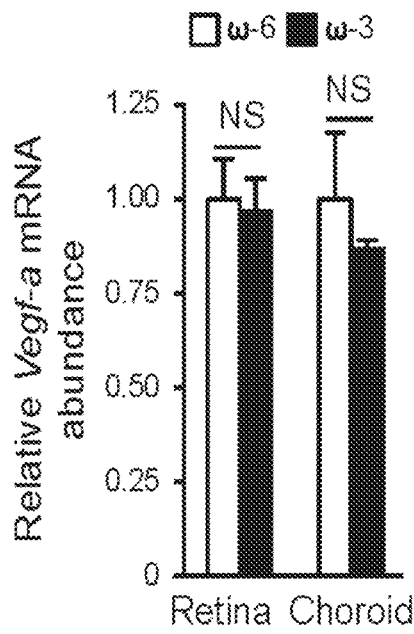
FIGS. 7A-C. Dietary ω-3 LCPUFA intervention suppresses VEGF expression in the retina and choroid. (A) Real-time PCR analysis of Vegf-a mRNA was assessed 7-days after CNV induction in mice fed ω-6 or ω-3 LCPUFAs. Data are means±SEM (n=6). (B and C) ELISA of VEGF levels in the retina (B) and choroid (C) at 5- and 7-days after CNV induction in mice fed ω-6 or ω-3 LCPUFAs (n=6). Data are means±SEM **P<0.01.

Infiltrating macrophages and leukocytes could be a source of inflammatory cytokines (Ishida et al., Nat Med. 2003;9: 781-788) and proangiogenic molecules such as VEGF that contribute to CNV pathogenesis (Noda et al., Faseb J. 2008;22:2928-2935). To investigate whether VEGF associates with CNV resolution, VEGF expression was examined at the mRNA and protein levels. The amount of Vegf-a mRNA in the retina or choroid 7-days after CNV induction did not differ between mice fed ω-3 or ω-6 LCPUFA diets (FIG. 7A). The abundance of VEGF protein in both the retina and choroid at 7-days (but not at 5-days) after CNV

TABLE 2

Pressure drop (ΔP) and shear stress (τ) values for representative flow chamber experiments

| | P selectin | | | E selectin | | | ICAM-1 | | | Pselectin + ICAM-1 | | | P selectin + ICAM-1 ω-3 + | | |
|---|---|---|---|---|---|---|---|---|---|---|---|---|---|---|---|
| | ω-6 | ω-3 | P | ω-6 | ω-3 | P | ω-6 | ω-3 | P | | | | ω-3 | GW | P |
| ΔP (mmHg) | 26.46 | 25.23 | 0.34 | 25.58 | 25.36 | 0.77 | 25.70 | 25.11 | 0.32 | | | | 21.82 | 24.44 | 0.70 |
| τ (dyne/cm$^2$) | 14.10 | 13.45 | 0.34 | 13.64 | 13.52 | 0.77 | 13.70 | 13.39 | 0.32 | | | | 11.63 | 13.03 | 0.70 |

Example 7

Figure 7B:
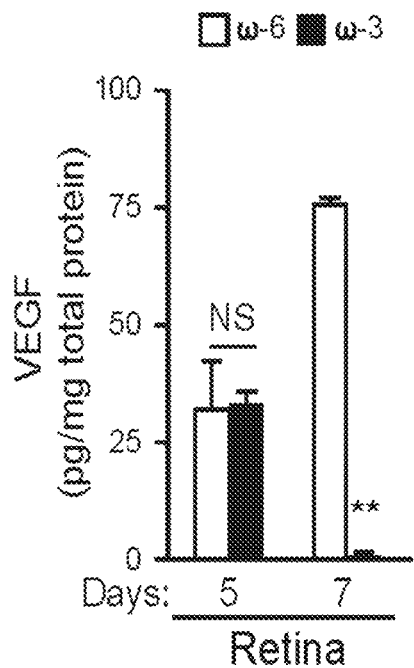
Figure 7C:
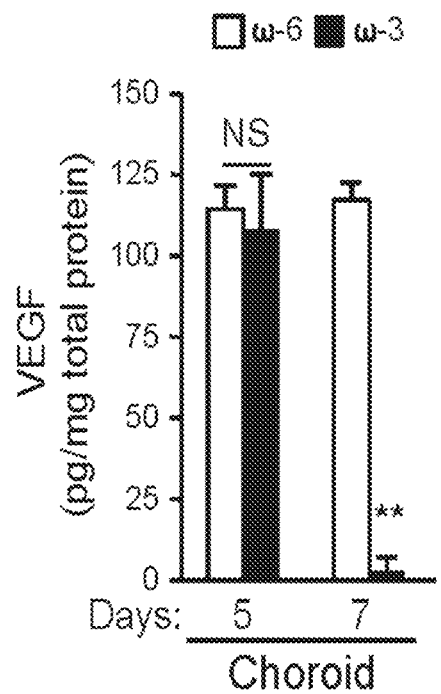
Figure 8:
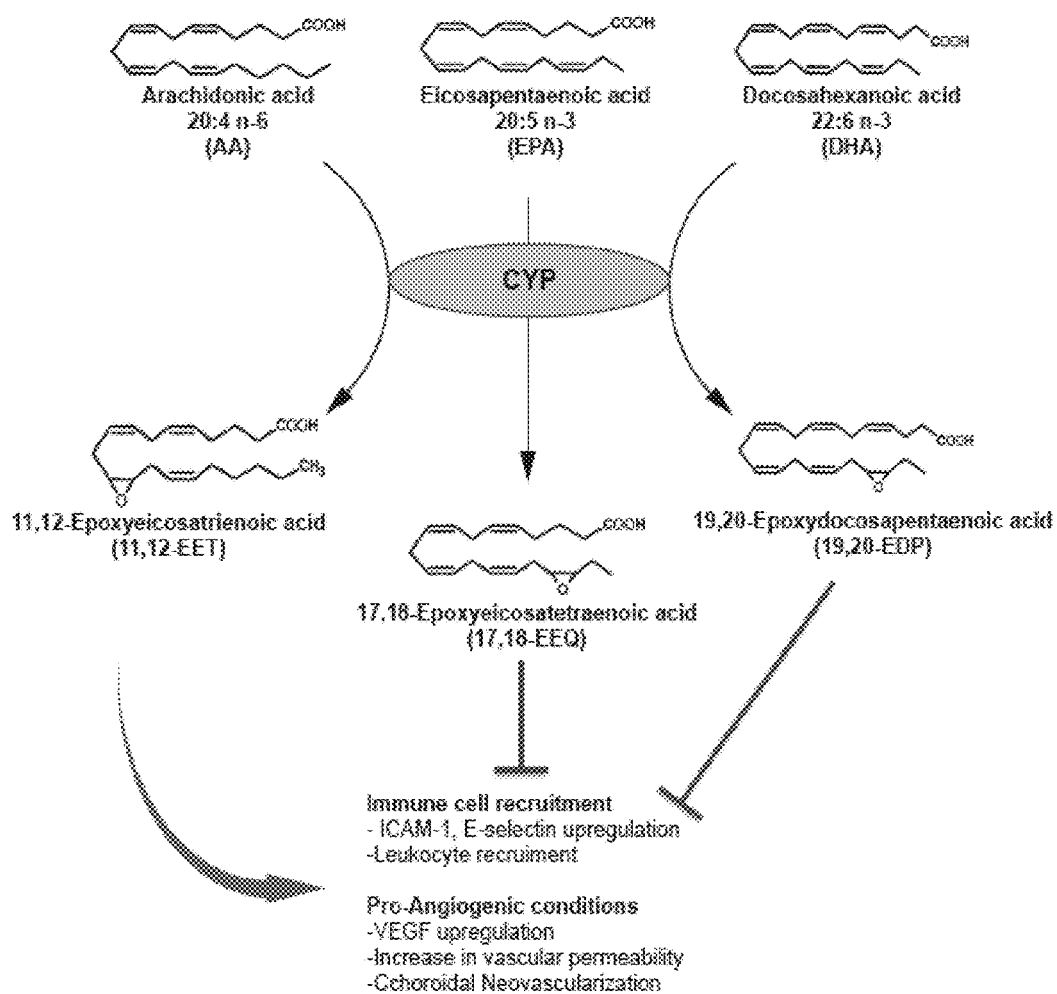
FIG. 8. Proposed roles of CYP-dependent lipid metabolites in Choroidal Neovascularization. AA, DHA and EPA, are liberated by phospholipase A2, and compete for conversion by the CYP-NADPH reductase complex that can function as hydroxylase or epoxygenases. EPA and DHA are efficient alternative substrates for the AA metabolizing CYP isoforms and reduced AA-derived 14,15-EET metabolite, while increasing both EPA derived 17,18-EEQ and DHA derived 19,20-EDP metabolites. These CYP metabolites derived from ω-3 LCPUFA promote choroidal neovessel resolution by down-regulating of the inflammatory conditions and pre-angiogenic conditions.

Invasion of Cx3Cr1 Positive Cells is Suppressed in the Choroid and Retina of CNV Lesions in ω-3 LCPUFAs Fed Mice Macrophages and leukocytes are a source of inflammatory cytokines and pro-angiogenic molecules such as VEGF that contribute to choroidal neovessel pathogenesis (Grossniklaus et al., Mol Vis. 2002;8:119-126). Previous studies reported inflammatory cell invasion in surgically excised CNV lesions from AMD patients as well as in postmortem CNV eyes (Noda et al., supra). To investigate if down-regulation of leukocyte adhesion molecules during ω-3 LCPUFA intervention affects leukocyte infiltration in the eye, the number of leukocytes in the retina and choroid was quantified after CNV induction using $Cx3cr1^{GFP/+}$ mice (Ishida et al, supra). $Cx3cr1^{GFP/+}$ mice fed an ω-3-diet, manifested significantly fewer leukocytes in the retina (FIG. 6A) and choroid (FIG. 6B) compared with ω-6-fed induction was significantly reduced in ω-3-fed mice compared ω-6 fed mice (FIGS. 7B and C). This pattern of VEGF expression correlated closely with CNV size and vessel leakage (FIG. 1), and indicates that modulation of ocular angiogenesis and immune cell infiltration by ω-3 LCPUFAs contributes to their protective effect against CNV.

Example 9

Supplementation with Metabolites Decreases Inflammation

While dietary ω-3 LCPUFAs are effective in reducing VEGF expression and protect against CNV, administration of metabolites might provide a more potent therapeutic effect. Thus the effect of EEQ and EDP derived metabolites on leucocyte rolling was evaluated as described above.

The EEQ and EDP derived metabolites described herein decreased leucocyte recruitment to the lesion site by increasing rolling velocity in these animals (FIGS. 9A and B), and thus are anti-inflammatory; the omega-6 derived EETs did not. In contrast, the omega-6 derived EETs further decreased rolling velocity on ICAM coated flow chambers in comparison with the EEQ and EDP derived metabolites (FIGS. 9C and D), implicating them in immune cell recruitment and a pro-inflammatory phenotype. Thus administration of 17,18-EEQ and 19,20-EDP reduces systemic leukocyte recruitment during CNV.

Figure 9G:
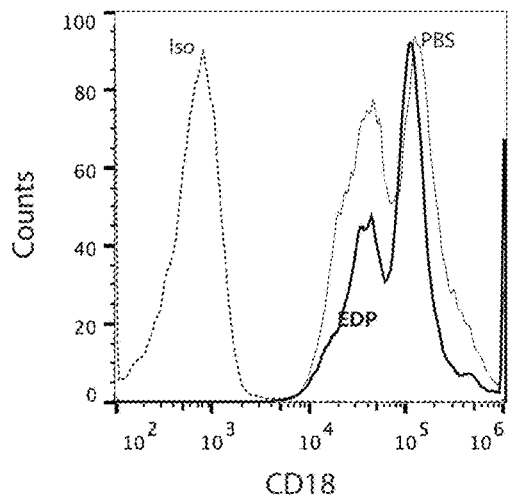
Figure 9H:
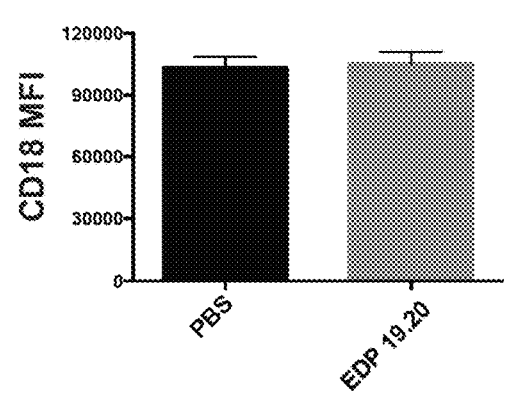
Figure 9I:
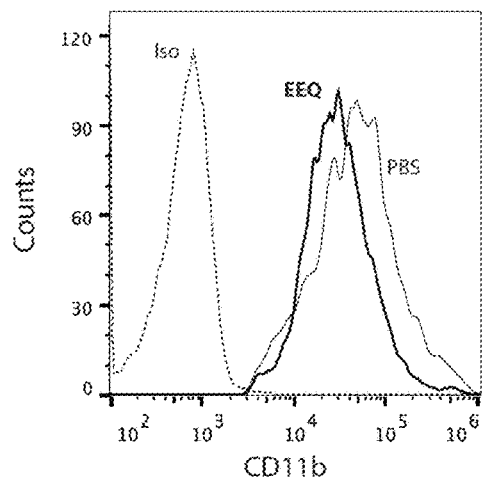
Figure 9J:
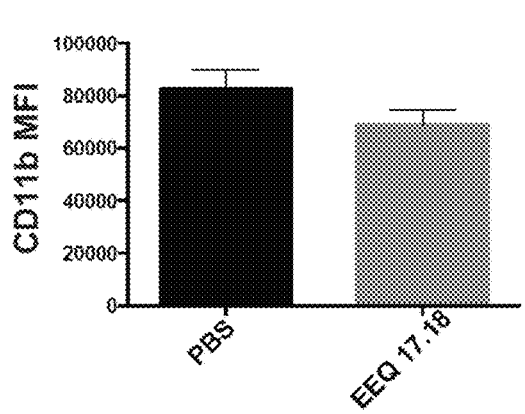
Figures 9K, 9L:
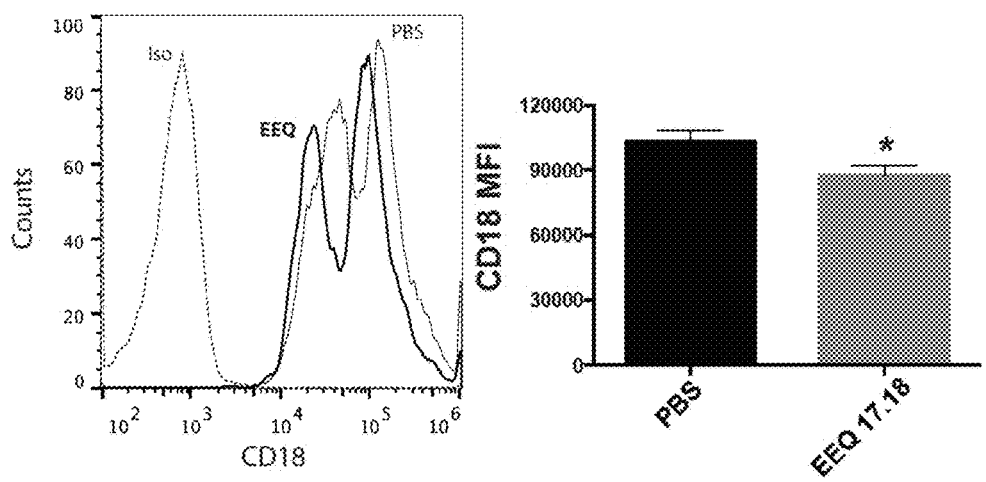

The effects of dietary ω-3-LCPUFA metabolites on adhesion molecule expression were examined in the laser-induced CNV model. Each metabolite seemed to have a different effect on a specific ICAM ligand. EDP suppresses CD11b in peripheral blood leukocytes (FIGS. 9E-F) but not CD18 (FIGS. 9G-H), whereas EEQ suppresses CD18 in peripheral blood leukocytes (FIGS. 9K-L) but not CD11b (FIGS. 9I-J).

REFERENCES

1. Lim, L. S. et al. Age-related macular degeneration. Lancet. 379, 1728-1738 (2012).
2. Zhang, K., Zhang, L. & Weinreb, R. N. Ophthalmic drug discovery: novel targets and mechanisms for retinal diseases and glaucoma. Nat. Rev. Drug Discov. 11, 541-559 (2012).
3. Friedman, D. S. et al. Prevalence of age-related macular degeneration in the United States. Arch. Ophthalmol. 122, 564-572 (2004).
4. SanGiovanni, J. P. et al. The relationship of dietary lipid intake and age-related macular degeneration in a case-control study: AREDS Report No. 20. Arch. Ophthalmol. 125, 671-679 (2007).
5. SanGiovanni, J. P. et al. The relationship of dietary omega-3 long-chain polyunsaturated fatty acid intake with incident age-related macular degeneration: AREDS report no. 23. Arch. Ophthalmol. 126, 1274-1279 (2008).
6. Chew, E. Y. Fatty acids and retinopathy. N. Engl. J. Med. 364, 1970-1971 (2011).
7. Sangiovanni, J. P. et al. ω-3 Long-chain polyunsaturated fatty acid intake and 12-y incidence of neovascular age-related macular degeneration and central geographic atrophy: AREDS report 30, a prospective cohort study from the Age-Related Eye Disease Study. Am. J. Clin. Nutr. 90, 1601-1607 (2009).
8. Bhutto, I. & Lutty, G. Understanding age-related macular degeneration (AMD): relationships between the photoreceptor/retinal pigment epithelium/Bruch's membrane/choriocapillaris complex. Mol. Aspects Med. 33, 295-317 (2012).
9. Guyer, D. R. et al. Subfoveal choroidal neovascular membranes in age-related macular degeneration. Visual prognosis in eyes with relatively good initial visual acuity. Arch. Ophthalmol. 104, 702-705 (1986).
10. Wang, L. et al. Abundant lipid and protein components of drusen. PLoS One. 5, e10329 (2010).
11. Curcio, C. A., Rudolf, M. & Wang, L. Histochemistry and lipid profiling combine for insights into aging and age-related maculopathy. Methods Mol. Biol. 580, 267-281 (2009).
12. Wong, T. Y. et al. Prevalence and causes of low vision and blindness in an urban Malay population: the Singapore Malay Eye Study. Arch. Ophthalmol. 126, 1091-1099 (2008).
13. Gragoudas, E. S., Adamis, A. P., Cunningham, E. T., Jr., Feinsod, M. & Guyer, D. R. Pegaptanib for neovascular age-related macular degeneration. N. Engl. J. Med. 351, 2805-2816 (2004).
14. Ng, E. W. & Adamis, A. P. Anti-VEGF aptamer (pegaptanib) therapy for ocular vascular diseases. Ann. N. Y. Acad. Sci. 1082, 151-171 (2006).
15. Rosenfeld, P. J. et al. Ranibizumab for neovascular age-related macular degeneration. N. Engl. J. Med. 355, 1419-1431 (2006).
16. Sapieha, P. et al. 5-Lipoxygenase metabolite 4-HDHA is a mediator of the antiangiogenic effect of omega-3 polyunsaturated fatty acids. Sci. Transl. Med. 3, 69ra12 (2011).
17. Connor, K. M. et al. Increased dietary intake of omega-3-polyunsaturated fatty acids reduces pathological retinal angiogenesis. Nat. Med. 13, 868-873 (2007).
18. Bazan, N. G. Homeostatic regulation of photoreceptor cell integrity: significance of the potent mediator neuroprotectin D1 biosynthesized from docosahexaenoic acid: the Proctor Lecture. Invest. Ophthalmol. Vis. Sci. 48, 4866-4881 (2007).
19. Stahl, A. et al. Short communication: PPAR gamma mediates a direct antiangiogenic effect of omega 3-PUFAs in proliferative retinopathy. Circ. Res. 107, 495-500 (2010).
20. Kang, J. X. et al. The role of the tissue omega6/omega-3 fatty acid ratio in regulating tumor angiogenesis. Cancer Metast. Rev. In press.
21. Sheets K. G. et al. Neuroprotectin D1 attenuates laser-induced choroidal neovascularization in mouse. Mol Vis. 16, 320-329 (2010).
22. SanGiovanni, J. P. & Chew, E. Y. The role of omega-3 long-chain polyunsaturated fatty acids in health and disease of the retina. Prog. Retin. Eye Res. 24, 87-138 (2005).
23. Montezuma, S. R., Vavvas, D. & Miller, J. W. Review of the ocular angiogenesis animal models. Semin. Ophthalmol. 24, 52-61 (2009).
24. Afzal, A. et al. Targeting retinal and choroid neovascularization using the small molecule inhibitor carboxyamidotriazole. Brain Res. Bull. 81, 320-326 (2010).
25. Giani, A. et al. Spectral-domain optical coherence tomography as an indicator of fluorescein angiography leakage from choroidal neovascularization. Invest. Ophthalmol. Vis. Sci. 52, 5579-5586 (2011).
26. Sulzbacher, F. et al. Correlation of SD-OCT features and retinal sensitivity in neovascular age-related macular degeneration. Invest. Ophthalmol. Vis. Sci. 53, 6448-6455 (2012).
27. Arnold, C., Konkel, A., Fischer, R. & Schunck, W. H. Cytochrome P450-dependent metabolism of omega-6 and omega-3 long-chain polyunsaturated fatty acids. Pharmacol. Rep. 62, 536-547 (2010).
28. Arnold, C. et al. Arachidonic acid-metabolizing cytochrome P450 enzymes are targets of ω-3 fatty acids. J. Biol. Chem. 285, 32720-32733 (2010).
29. Konkel, A. & Schunck, W. H. Role of cytochrome P450 enzymes in the bioactivation of polyunsaturated fatty acids. Biochim. Biophys. Acta 1814, 210-222 (2011).
30. Serhan, C. N. & Devchand, P. R. Novel antiinflammatory targets for asthma. A role for PPARgamma? Am. J. Respir. Cell Mol. Biol. 24, 658-661 (2001).
31. Ambati, J. & Fowler, B. J. Mechanisms of age-related macular degeneration. Neuron 75, 26-39 (2012).
32. Noda, K. et al. Vascular adhesion protein-1 blockade suppresses choroidal neovascularization. FASEB J. 22, 2928-2935 (2008).
33. Almulki, L. et al. Surprising up-regulation of P-selectin glycoprotein ligand-1 (PSGL-1) in endotoxin-induced uveitis. FASEB J. 23, 929-939 (2009).

34. Cherepanoff, S., McMenamin, P., Gillies, M. C., Kettle, E. & Sarks, S. H. Bruch's membrane and choroidal macrophages in early and advanced age-related macular degeneration. Br. J. Ophthalmol. 94, 918-925 (2010).
35. Zarbin, M. A. Current concepts in the pathogenesis of age-related macular degeneration. Arch. Ophthalmol. 122, 598-614 (2004).
36. Ishida, S. et al. Leukocytes mediate retinal vascular remodeling during development and vaso-obliteration in disease. Nat. Med. 9, 781-788 (2003).
37. Daviglus, M. L. et al. Fish consumption and the 30-year risk of fatal myocardial infarction. N Engl J Med. 336, 1046-1053 (1997).
38. Berson, E. L., Rosner, B., Sandberg, M. A., Weigel-DiFranco, C. & Willett, W. C. ω-3 intake and visual acuity in patients with retinitis pigmentosa receiving vitamin A. Arch. Ophthalmol. 130, 707-711 (2012).
39. Miles, E. A. & Calder, P. C. Influence of marine n-3 polyunsaturated fatty acids on immune function and a systematic review of their effects on clinical outcomes in rheumatoid arthritis. Br. J. Nutr. 107 (suppl. 2), S171-S184 (2012).
40. Simopoulos AP Omega-3 fatty acids in inflammation and autoimmune diseases. *J Am. Coll. Nutr.* 21, 495-505 (2002)
41. Nakai, K. et al. Dendritic cells augment choroidal neovascularization. *Invest. Ophthalmol. Vis. Sci.* 49, 3666-3670 (2008).
42. Marneros, A. G. Endogenous endostatin inhibits choroidal neovascularization. *FASEB J.* 21, 3809-3818 (2007).
43. Hafezi-Moghadam, A., Thomas, K. L. & Cornelssen, C. A novel mouse-driven ex vivo flow chamber for the study of leukocyte and platelet function. *Am. J. Physiol. Cell Physiol.* 286, C876-C892 (2004).

Other Embodiments

It is to be understood that while the invention has been described in conjunction with the detailed description thereof, the foregoing description is intended to illustrate and not limit the scope of the inited Statesnvention, which is defined by the scope of the appended claims. Other aspects, advantages, and modifications are within the scope of the following claims.

What is claimed is:

1. A method for treating or reducing risk of a disorder associated with vascular leakage in a subject, the method comprising:
   identifying a subject who has or is at risk of developing a disorder associated with vascular leakage in a subject; and
   administering to the identified subject a therapeutically effective amount of a pharmaceutical composition comprising 17, 18-EEQ and a pharmaceutically acceptable carrier, wherein the disorder is stroke.
2. The method of claim 1, wherein the composition further comprises 19,20-EDP.
3. The method of claim 2, wherein the 17,18-EEQ and/or 19,20-EDP is substantially purified.

* * * * *

UNITED STATES PATENT AND TRADEMARK OFFICE
CERTIFICATE OF CORRECTION

PATENT NO. : 10,413,518 B2  
APPLICATION NO. : 15/684251  
DATED : September 17, 2019  
INVENTOR(S) : Kip M. Connor and Ryoji Yanai Page 1 of 1

It is certified that error appears in the above-identified patent and that said Letters Patent is hereby corrected as shown below:

On the Title Page

In Column 1, Line 18 (approx.), after (*) Notice paragraph, insert -- (*) Notice: This patent is subject to a terminal disclaimer. --

In the Specification

In Column 1, Line 6, delete "continuation" and insert -- divisional --

In Column 1, Line 8, after "2015," insert -- now U.S. Patent No. 9,770,426, --

Signed and Sealed this  
Thirteenth Day of October, 2020

Andrei Iancu  
*Director of the United States Patent and Trademark Office*